US011594327B2

(12) United States Patent
Kubo et al.

(10) Patent No.: US 11,594,327 B2
(45) Date of Patent: Feb. 28, 2023

(54) INFORMATION PROCESSING APPARATUS, INFORMATION PROCESSING METHOD, AND RECORDING MEDIUM

(71) Applicant: CANON KABUSHIKI KAISHA, Tokyo (JP)

(72) Inventors: Takeshi Kubo, Kyoto (JP); Gakuto Aoyama, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 492 days.

(21) Appl. No.: 15/845,934

(22) Filed: Dec. 18, 2017

(65) Prior Publication Data

US 2018/0182485 A1 Jun. 28, 2018

(30) Foreign Application Priority Data

Dec. 28, 2016 (JP) ............................. JP2016-256153

(51) Int. Cl.
*G16H 40/63* (2018.01)
*G16H 30/40* (2018.01)
*A61B 5/00* (2006.01)

(52) U.S. Cl.
CPC ........... *G16H 40/63* (2018.01); *A61B 5/7425* (2013.01); *A61B 5/7445* (2013.01); *G16H 30/40* (2018.01)

(58) Field of Classification Search
CPC ...... G16H 40/63; G16H 30/40; A61B 5/7425; A61B 5/7445; A61B 8/463; A61B 8/465; A61B 5/7435; G06F 3/048
USPC ........................................................ 705/2–3
See application file for complete search history.

(56) References Cited

U.S. PATENT DOCUMENTS

| 9,092,458 | B1* | 7/2015 | Perona | G06F 16/5838 |
| 2007/0286469 | A1* | 12/2007 | Yamagata | G06T 7/0012 |
| | | | | 382/131 |
| 2009/0028403 | A1* | 1/2009 | Bar-Aviv | G06K 9/46 |
| | | | | 382/128 |
| 2009/0080734 | A1* | 3/2009 | Moriya | G06F 19/321 |
| | | | | 382/128 |
| 2013/0141462 | A1* | 6/2013 | Niwa | G06F 3/0485 |
| | | | | 345/634 |
| 2014/0310592 | A1* | 10/2014 | Melton | G06F 16/986 |
| | | | | 715/234 |

(Continued)

FOREIGN PATENT DOCUMENTS

| JP | H10-240914 A | 9/1998 |
| JP | 2006-271541 A | 10/2006 |

(Continued)

*Primary Examiner* — Joseph D Burgess
(74) *Attorney, Agent, or Firm* — Canon U.S.A., Inc. IP Division

(57) ABSTRACT

An information processing apparatus includes a first acquisition unit that acquires a user's instruction to change medical information to be displayed on a display unit, a second acquisition unit that acquires a plurality of pieces of medical information to be sequentially displayed on the display unit, a group generation unit that groups the acquired plurality of pieces of medical information based on the acquired user's instruction, a third acquisition unit configured to acquire representative information indicating the medical information contained in the group generated by the group generation unit, and an output unit configured to output the acquired representative information to the display unit.

18 Claims, 18 Drawing Sheets

(56) References Cited

U.S. PATENT DOCUMENTS

| | | | | |
|---|---|---|---|---|
| 2015/0157284 A1* | 6/2015 | Kim | ............... | A61B 6/502 |
| | | | | 715/838 |
| 2015/0199121 A1* | 7/2015 | Gulaka | ............... | G16H 40/63 |
| | | | | 715/771 |
| 2015/0363053 A1* | 12/2015 | Aoyama | ............... | G06F 3/0482 |
| | | | | 715/838 |
| 2017/0300664 A1* | 10/2017 | Matsuki | ............... | G16H 30/20 |
| 2019/0133425 A1* | 5/2019 | Taniguchi | ............... | G16H 30/20 |

FOREIGN PATENT DOCUMENTS

| | | |
|---|---|---|
| JP | 2011-254904 A | 12/2011 |
| JP | 2012-114559 A | 6/2012 |
| JP | 2012-120695 A | 6/2012 |
| JP | 2016-001372 A | 1/2016 |
| WO | 2011/013475 A1 | 2/2011 |

* cited by examiner

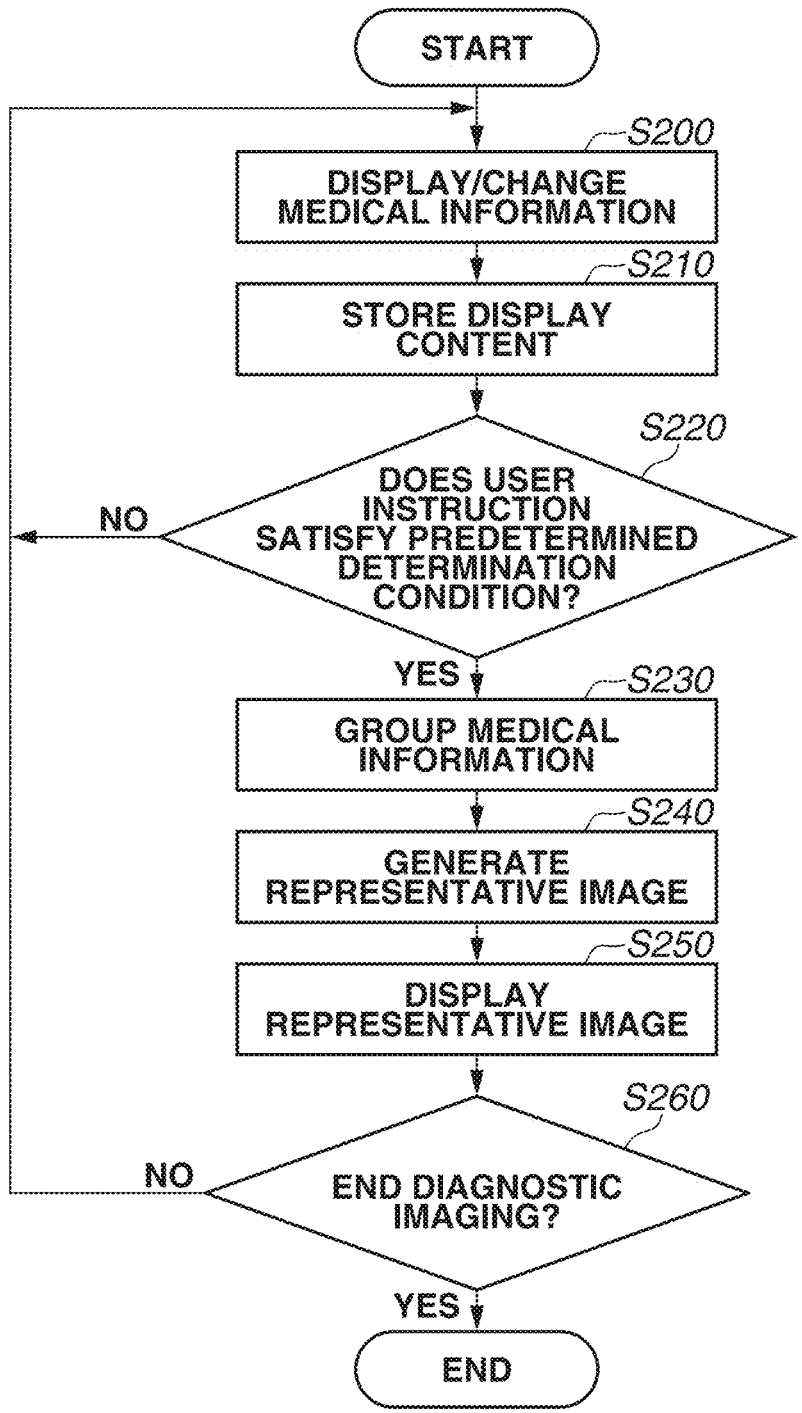

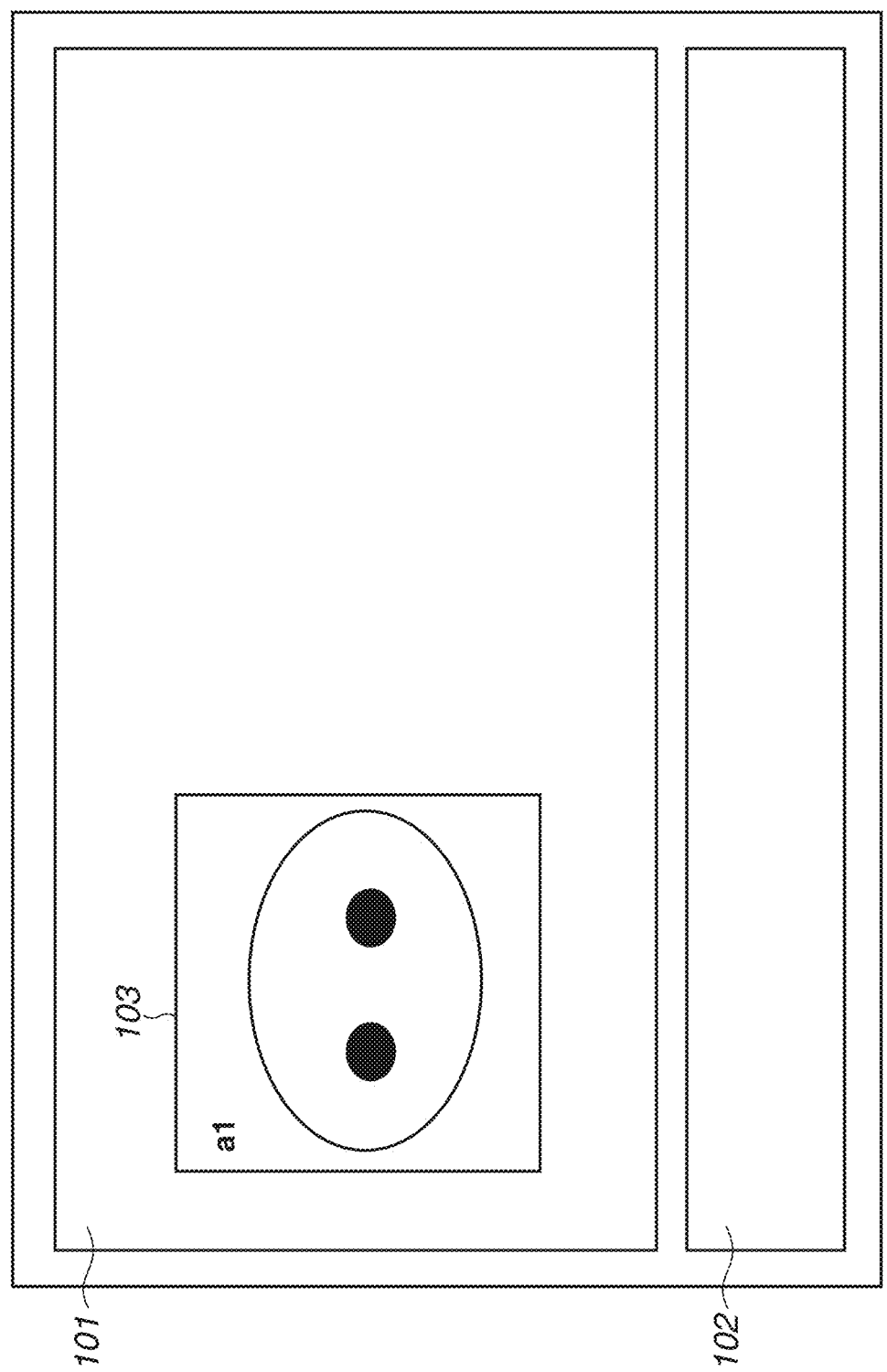

FIG.5

| CAPTURE IMAGE | DISPLAY TIME PERIOD |
|---|---|
| INSTRUCTION TO DISPLAY MEDICAL IMAGE 103 (INSTRUCTION ISSUED FOR THE FIRST TIME) ||
| a1 | ONE SECOND |
| INSTRUCTION TO CARRY OUT FUNCTION OF ADVANCING TO NEXT SLICE (a1 to a2) ||
| a2 | THREE SECONDS |
| INSTRUCTION TO CARRY OUT FUNCTION OF ADVANCING TO NEXT SLICE (a2 to a3) ||
| a3 | TWO SECONDS |
| INSTRUCTION TO CHANGE OBSERVATION TARGET TO MEDICAL IMAGE 104 || inf200, inf210, inf220

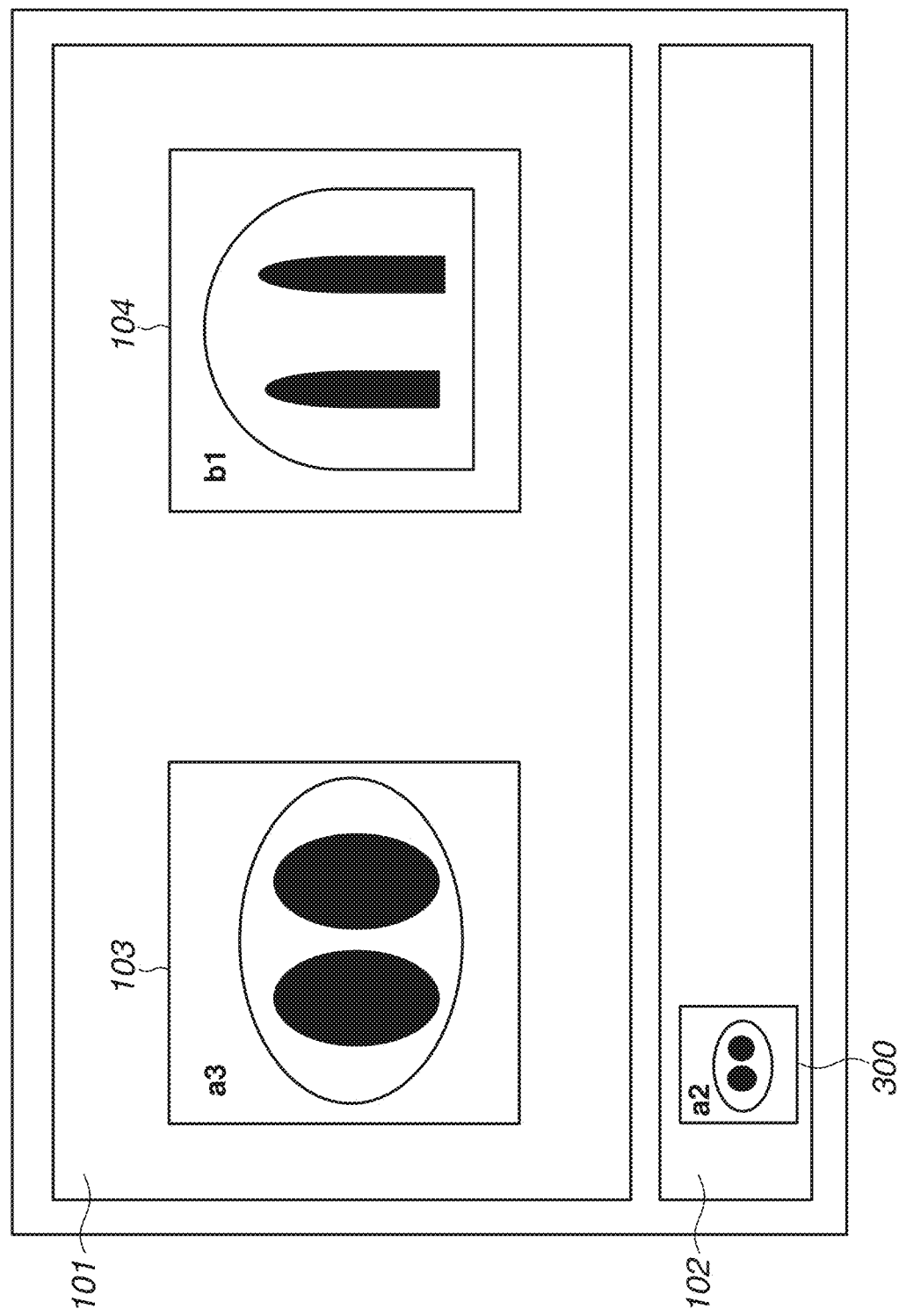

FIG.7

| CAPTURE IMAGE | DISPLAY TIME PERIOD |
|---|---|
| INSTRUCTION TO DISPLAY MEDICAL IMAGE 103 (INSTRUCTION ISSUED FOR THE FIRST TIME) ||
| inf200 — a1 | ONE SECOND |
| INSTRUCTION TO CARRY OUT FUNCTION OF ADVANCING TO NEXT SLICE (a1 to a2) ||
| inf210 — a2 | THREE SECONDS |
| INSTRUCTION TO CARRY OUT FUNCTION OF ADVANCING TO NEXT SLICE (a2 to a3) ||
| inf220 — a3 | TWO SECONDS |
| INSTRUCTION TO CHANGE OBSERVATION TARGET TO MEDICAL IMAGE 104 ||
| inf230 — b1 | TWO SECONDS |
| INSTRUCTION TO CARRY OUT FUNCTION OF ADVANCING TO NEXT SLICE (b1 to b2) ||
| inf240 — b2 | SIX SECONDS |
| INSTRUCTION TO CARRY OUT DENSITY CONVERSION FUNCTION ||

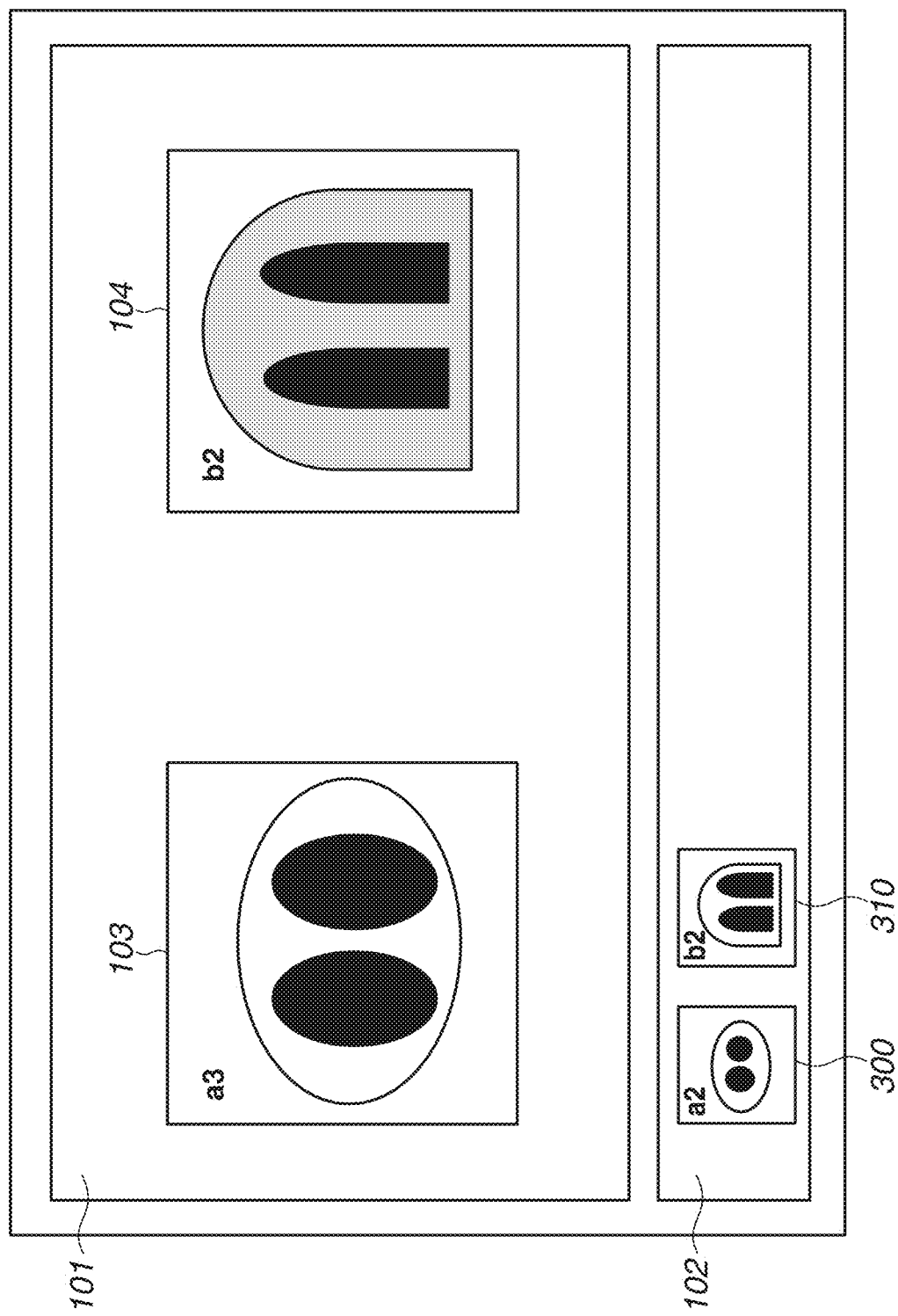

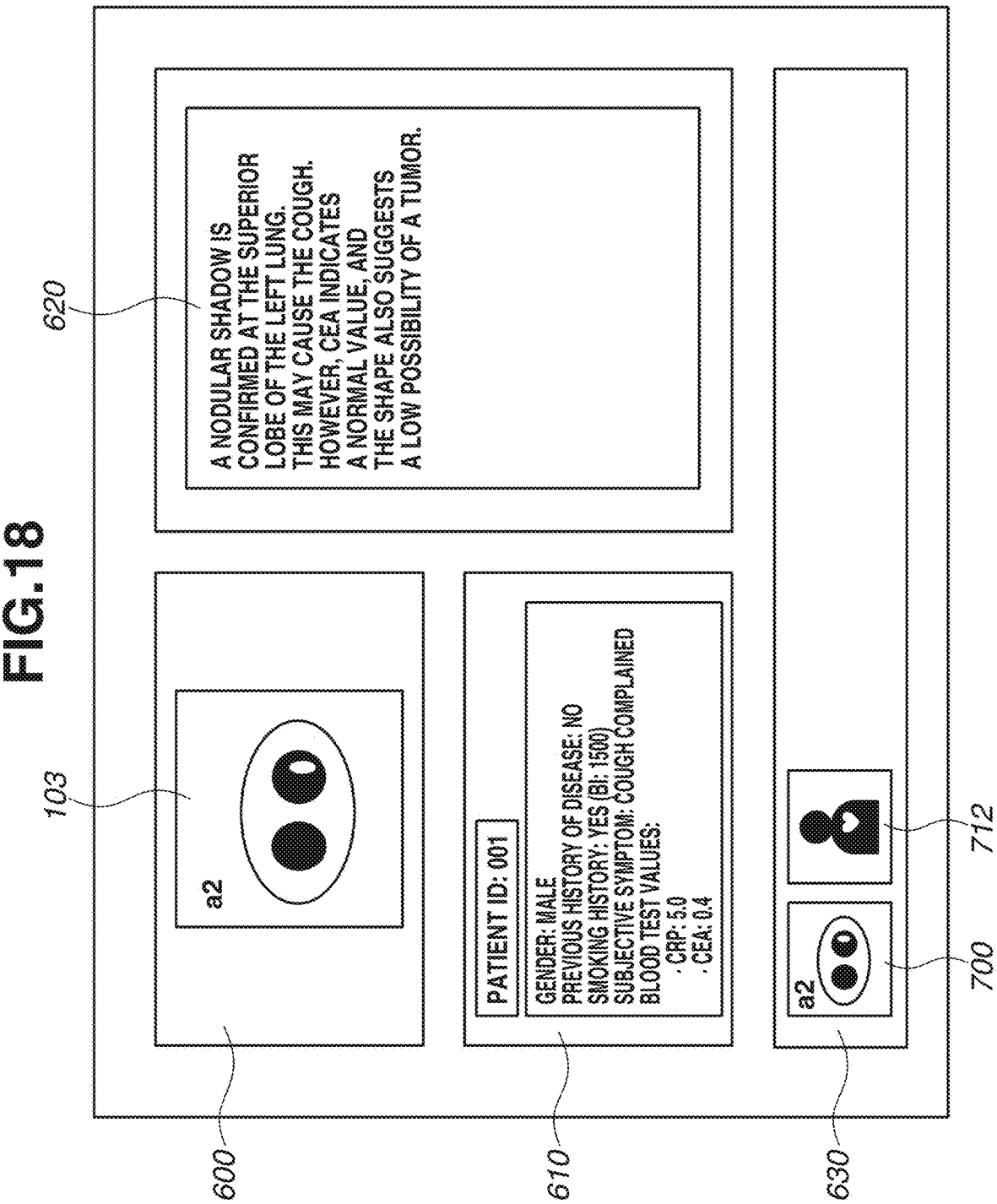

INFORMATION PROCESSING APPARATUS, INFORMATION PROCESSING METHOD, AND RECORDING MEDIUM

BACKGROUND

Field

The disclosure of the present specification relates to an information processing apparatus, an information processing method, and a recording medium.

Description of the Related Art

Diagnostic imaging carried out by a medical doctor typically includes a plurality of work processes, where the medical doctor carries out the diagnostic imaging while appropriately switching information to utilize according to each of the work processes. For example, for a medical image of a truncal site, first, the medical doctor observes a lung field region after switching a condition under which the medical image is displayed (a density conversion parameter or the like) to a condition suitable to detect an abnormality in the lung region. If an abnormality is found in the observed region, the medical doctor enlarges the region containing the abnormality and observes it in detail. Next, the medical doctor observes a liver region after switching the display condition to a display condition suitable to detect an abnormality in the liver region. The medical doctor can then observe a bone region after switching the display condition to a display condition suitable to detect an abnormality in the bone region. The medical doctor confirms appropriately information written in an electronic medical record.

To allow the medical doctor to confirm the already performed work process in the diagnostic imaging including such complicated work processes, International Publication No. 2011/013475 discusses chronologically presenting an image indicating information about the operation performed by the medical doctor regarding the diagnostic imaging.

The technique discussed in International Publication No. 2011/013475 only displays an abstract image of the operation performed by the medical doctor, and does not allow a user to confirm the work process as detailed as a display manner and/or a display content of the information utilized in each of the work processes. Therefore, the user cannot correctly recognize the work process performed until that time (a work history) in the diagnostic imaging.

SUMMARY

According to an aspect of the present invention, an information processing apparatus includes a first acquisition unit configured to acquire a user's instruction to change medical information to be displayed on a display unit, a second acquisition unit configured to acquire a plurality of pieces of medical information to be sequentially displayed on the display unit, a group generation unit configured to group the acquired plurality of pieces of medical information based on the acquired user's instruction, a third acquisition unit configured to acquire representative information indicating the medical information contained in the group generated by the group generation unit, and an output unit configured to output the acquired representative information to the display unit.

Further features will become apparent from the following description of exemplary embodiments with reference to the attached drawings.

BRIEF DESCRIPTION OF THE DRAWINGS

FIG. 2 is a flowchart illustrating an example of overall processing according to the exemplary embodiment.

FIG. 3 illustrates a screen example after medical information is displayed according to the exemplary embodiment.

FIG. 5 illustrates how an example of reproduction information stored by a display content storage unit looks like.

FIG. 6 illustrates a screen example after a representative image is displayed according to the exemplary embodiment.

FIG. 7 illustrates how an example of the reproduction information stored by the display content storage unit looks like.

FIG. 8 illustrates a screen example after a representative image of a second group is displayed according to the exemplary embodiment.

FIG. 18 illustrates a screen example after the representative image of the second group is displayed according to the exemplary modification 5.

DESCRIPTION OF THE EMBODIMENTS

In the following description, an example of an exemplary embodiment will be described with reference to the accompanying drawings. The configuration described in the following exemplary embodiment is merely an example, is not seen to be limiting.

The disclosure of the present specification is directed to providing an information processing apparatus and an information processing method enabling users to correctly confirm the work process performed in a diagnostic imaging task.

Figure 1:
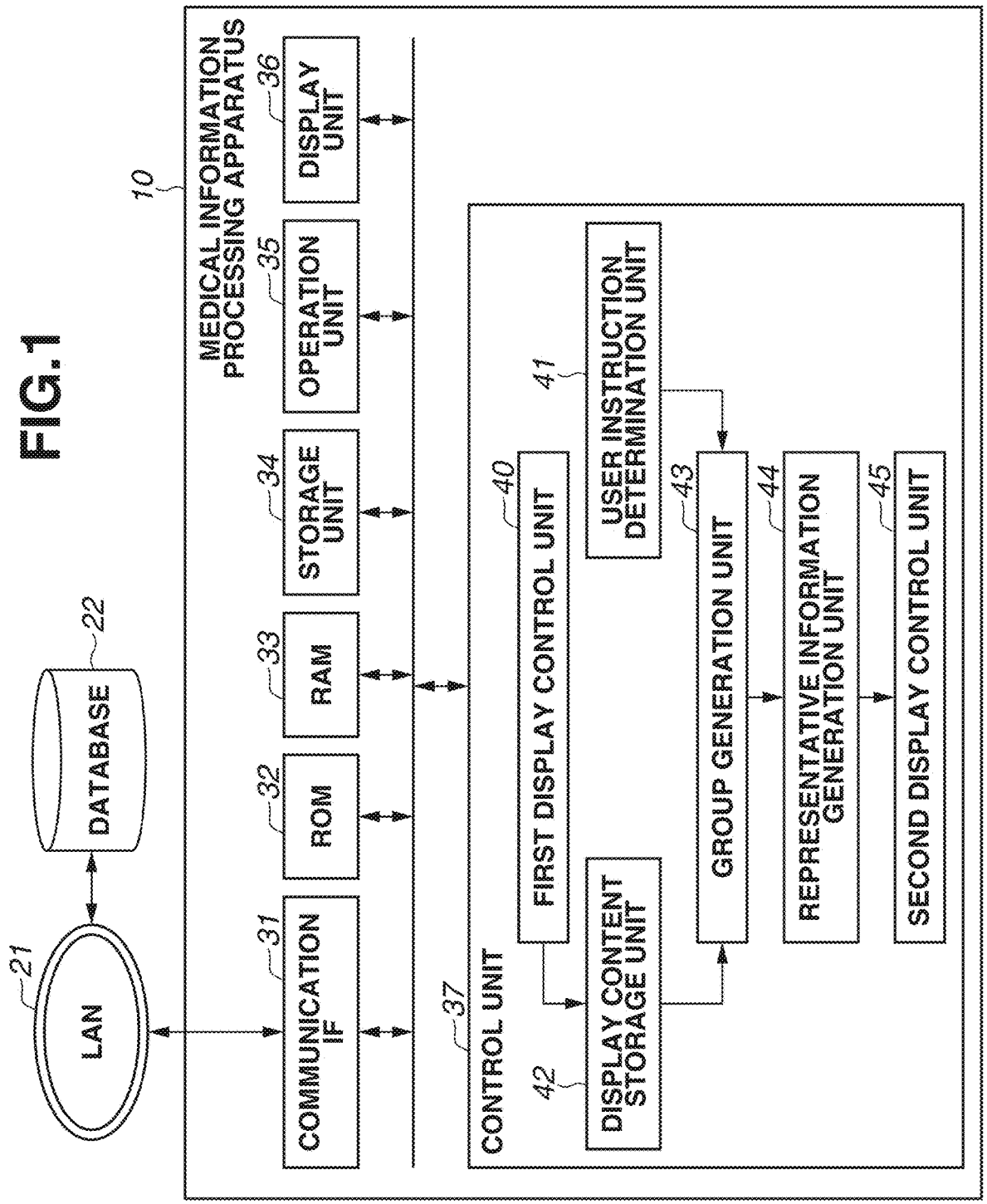
FIG. 1 is a block diagram illustrating an example of a configuration of a medical information processing system according to an exemplary embodiment.

FIG. 1 illustrates one example of an overall configuration of a medical information processing system including a medical information processing apparatus according to the present exemplary embodiment.

The medical information processing system includes a medical information processing apparatus 10 and a database 22, which communicate with each other via a communication unit. In the present exemplary embodiment, an example of the communication unit a local area network (LAN) 21.

The database 22 manages medical images captured by medical image capturing apparatus (not illustrated), and various kinds of examination information recorded by an electronic medical record system, a hospital information system (HIS), a radiology information system (RIS), and/or the like. Hereinafter, the information utilized in the diagnostic imaging task, such as the medical image and the examination information, will be referred to as "medical information". The medical information processing apparatus 10 acquires the medical information managed by the database 22 via the LAN 21.

The medical information processing apparatus 10 includes a communication interface (IF) 31, a read only memory (ROM) 32, a random access memory (RAM) 33, a storage unit 34, an operation unit 35, a display unit 36, and a control unit 37 as a functional configuration thereof.

The communication IF 31 is realized by, for example, a LAN card, and is communication medium between an external apparatus (for example, the database 22) and the medical information processing apparatus 10 via the LAN 21. The ROM 32 is realized by, for example, a nonvolatile memory, and stores various kinds of programs and the like therein. The RAM 33 is realized by, for example, a volatile memory, and temporarily stores various kinds of information therein. The storage unit 34 is realized by, for example, a hard disk drive (HDD), and stores various kinds of information therein. The operation unit 35 is realized by, for example, a keyboard and a mouse, and provides an instruction from the user to the apparatus. The display unit 36 is realized by, for example, a display, and displays various kinds of information for the user (for example, a medical doctor).

The control unit 37 is realized by, for example, a central processing unit (CPU), and controls processing in the medical information processing apparatus 10. The control unit 37 includes a first display control unit 40, a user instruction determination unit 41, a display content storage unit 42, a group generation unit 43, a representative information generation unit 44, and a second display control unit 45 as a functional configuration thereof. The CPU executes the program stored in the ROM 32 to function as the first display control unit 40, the user instruction determination unit 41, the display content storage unit 42, the group generation unit 43, the representative information generation unit 44, and the second display control unit 45.

The medical information processing apparatus 10 can include one CPU and one ROM or can include a plurality of CPUs and a plurality of ROMs. In other words, at least one or more processor(s) and at least one or more memory(ies) are connected, and the CPU functions as each of the above-described units when the at least one or more processor(s) execute(s) the program stored in the at least one or more memory(ies). The processing device is not be limited to the CPU, and can be a graphics processing unit (GPU) or the like.

The first display control unit 40 controls displaying the medical information on the display unit 36 based on the user's instruction. The first display control unit 40 reads out at least one piece of medical information selected by the user from the database 22 using the operation unit 35, and displays the read information on the display unit 36. The first display control unit 40 changes a display content of the medical information on the display unit 36 based on the user's instruction issued using the operation unit 35. The first display control unit 40 outputs the display content displayed by the first display control unit 40 to the display content storage unit 42. The display content will be specifically described below.

The user instruction determination unit 41 sequentially acquires the user's instruction directed to the first display control unit 40, and determines whether this instruction satisfies a predetermined determination condition. Then, the user instruction determination unit 41 outputs a result of the determination to the group generation unit 43. The predetermined determination condition refers to a condition based on a determination about, for example, whether the user's instruction is an instruction serving to separate work processes. The determination condition will be specifically described below.

The user instruction determination unit 41 corresponds to an example of a first acquisition unit configured to acquire a user's instruction to change medical information to be displayed on a display unit.

The display content storage unit 42 acquires the display content displayed by the first display control unit 40, and stores information necessary to reproduce this display content (hereinafter referred to as reproduction information) into the storage unit 34 or the RAM 33. The reproduction information will be specifically described below. The display content storage unit 42 outputs the stored reproduction information to the group generation unit 43. The display content storage unit 42 corresponds to an example of a second acquisition unit configured to acquire a plurality of pieces of medical information that is to be sequentially displayed on the display unit.

The group generation unit 43 reads out pieces of reproduction information regarding a series of display contents determined to belong to one work process based on the result of the determination by the user instruction determination unit 41 from the display content storage unit 42, and groups them. The group generation unit 43 outputs information about each grouped group to the representative information generation unit 44. The group generation unit 43 corresponds to an example of a group generation unit configured to group the plurality of pieces of medical information acquired by the second acquisition unit based on the user's instruction acquired by the first acquisition unit. For example, the group contains the medical information displayed on the display unit during a time period since receipt of the user's instruction to change the medical information until receipt of the user's instruction to change the above-described medical information again after that.

The representative information generation unit 44 generates information indicating the display content representative of each group generated by the group generation unit 43 (hereinafter referred to as representative information). The representative information refers to information representative of the plurality of display contents reproduced from the plurality of pieces of reproduction information in this group, and can be regarded as information representative of the series of display contents determined to belong to one certain work process (i.e., representing the work process on behalf thereof). The representative information generation unit 44 corresponds to one example of a third acquisition unit configured to acquire representative information indicating the medical information contained in the group generated by the group generation unit.

The representative information can be any kind of information as long as the user can easily recognize the content of the group. More specifically, the representative information is an image indicating the display content representative of the group (hereinafter referred to as a representative image), an icon or a mark simplifying the representative image, text information summarizing the representative information, or the like. In the following description, the present exemplary embodiment will be described assuming that the representative information is the representative image, but this is not seen to be limiting. The medical information processing apparatus 10 can be configured to be able to change the type of the representative information based on the user's instruction as appropriate. More specifically, the representative information including the representative image includes at least one of the medical information itself, a capture image of the medical information displayed on the display unit, and information generated by performing image processing on the medical information.

The second display control unit 45 controls displaying the representative information generated by the representative information generation unit 44 on the display unit 36. The second display control unit 45 corresponds to an example of an output unit configured to output the representative information acquired by the third acquisition unit to the display unit.

At least a part of the individual units included in the control unit 37 can be realized as an independent device. Alternatively, each of the units can be realized as software that achieves the function of the control unit 37. In this case, the software that achieves the function can operate on a server via a network, including a cloud. In the present exemplary embodiment, assume that the individual units are each realized by software under a local environment.

Next, an overall processing procedure performed by the control unit 37 according to the present exemplary embodiment will be described with reference to FIG. 2. FIG. 2 is a flowchart illustrating one example of the processing performed by the control unit 37.

In step S200, the first display control unit 40 reads out the medical information from the database 22 that was selected by the user using the operation unit 35, and displays the read medical information on the display unit 36. The first display control unit 40 sequentially changes the display content of the medical information on the display unit 36 based on the user's instruction issued using the operation unit 35. The user's instruction in the present exemplary embodiment refers to an instruction for operating the medical information processing apparatus 10 that is input by the user to the apparatus via the operation unit 35, and includes an instruction to carry out a function regarding the change in the display content. The user's instruction includes, for example, an "instruction to change the display image", an "instruction to carry out a density conversion function", or an "instruction to carry out a function of advancing to the next slice". The user's instruction to change the medical information includes an instruction to change a type of the medical information. The user's instruction to change the medical information includes one or more of an instruction to change contrast with respect to the medical image, an instruction to change a magnification ratio of the medical image, an instruction to change display of cross section of the medical image, and an instruction to change a type of the medical image.

In step S210, the display content storage unit 42 sequentially acquires the display content displayed by the first display control unit 40 in step S200, and sequentially stores the reproduction information of the display content in the storage unit 34 or the RAM 33. The reproduction information refers to the information that enables the acquired display content to be reproduced. An example of the reproduction information is data storing therein the content itself of the displayed information (hereinafter referred to as display information) and a display attribute in association with each other (hereinafter referred to as display information data). Another example is data generated by acquiring the content displayed on the screen as an image (hereinafter referred to as a capture image), a reduced image thereof, or the like. The display attribute is, for example, the type of the display information (information for identifying a text, a graphic, an image, or the like), a display position, a display layout, a range where the display information is acquired (in a case where the display information is only partially acquired) on the display unit 36, a color, a degree of transparency, and an enlargement ratio of each piece of display information. In the case where the display information is the text, the display attribute is, for example, a type and a size of a font.

The reproduction information can contain information regarding a result of displaying the display content. Th information is, for example, a time period during which this display content is displayed on the display unit 36 (hereinafter referred to as a display time period) or a time period during which the user observes this display content (hereinafter referred to as an observation time period). The reproduction information can contain the number of times that the user displays the display content or the number of times that the user observes the display content (hereinafter referred to as the number of observation times). The observation time period and the number of observation times can be measured by detecting information indicating the user's line of sight using a line-of-sight detection device (also called an eye tracking system) (not illustrated). The reproduction information does not necessarily need to be stored regarding all of the display contents. For example, the medical information processing apparatus 10 can be configured to not store a display content failing to satisfy a predetermined condition. An example of the predetermined condition include a condition that the display content should not be stored if the display time period of the display content falls below a predetermined time period, e.g., shorter than 0.5 seconds. The medical information processing apparatus 10 can be configured to not store a display content never likely to be selected by the representative information generation unit 44. For example, in a case where an employed criterion defines that a display content displayed for the longest time period should be selected, the present display content does not have to be stored if a display content displayed for a longer time period than the present display content is already stored in display contents belonging to the same group. To perform this processing, a start point of a grouping time period, which is described below with respect to step S230, should be calculated in this step in advance.

In step S220, the user instruction determination unit 41 sequentially acquires the user's instruction issued in step S200, and determines whether the acquired user's instruction (hereinafter referred to as a determination target instruction) satisfies the predetermined determination condition. For example, the condition based on the determination whether the user's instruction is the instruction serve to separate work processes can be used as the determination condition. Examples corresponding to this condition include a condition "the determination target instruction is an instruction to change an observation target", a condition "the determination target instruction is an instruction to carry out the density conversion function" (hereinafter referred to as a density conversion instruction), and a condition "the determination target instruction is an instruction to end the diagnostic imaging". A condition based on a determination that the user's instruction is an instruction indicating execution of a specific work process can be used as the determination condition. Examples corresponding to this condition include a condition "there is no instruction regarding the change in the display content for a predetermined time period or longer". The determination conditions described here are a mere examples and are not seen to be limiting. The determination condition can be set in advance or can be provided to be changeable by the user as appropriate. In a case where the determination target instruction satisfies the determination condition (YES in step S220), the processing proceeds to step S230. In a case where the determination target instruction does not satisfy the determination condition (NO in step S220), the processing returns to step S200.

In step S230, the group generation unit 43 extracts pieces of reproduction information stored during a predetermined time period from the pieces of reproduction information stored by the display content storage unit 42 based on a result of the determination in step S220. Then, the group generation unit 43 groups the extracted pieces of reproduction information as one group, and outputs the information thereof to the representative information generation unit 44. Assume that a start point and an end point of the predetermined time period during which the group generation unit 43 generates the group (hereinafter referred to as a grouping time period) is set based on predetermined criteria. More specifically, the criteria are set in such a manner that "the start point is an execution time point of the instruction that has satisfied the determination condition last time" and "the end point is a time point immediately before an execution time point of the instruction that has satisfied the determination condition this time". If complying with these criteria, in the present step, the group generation unit 43 acquires pieces of reproduction information stored during a time period since the "execution time point of the instruction that has satisfied the determination condition last time" until the "time point immediately before the execution time point of the instruction that has satisfied the determination condition this time", and groups them as one group.

The criteria for determining the grouping time period described here are an example and are not seen to be limiting. In other words, the medical information processing apparatus 10 can be configured to set the grouping time period using criteria different from the above-described criteria as long as the employed criteria are criteria that enable the display contents belonging to a certain work process to be grouped based on the determination result. For example, the criteria can be set in such a manner that "the start point is a time point thirty seconds after the execution time point of the instruction that has satisfied the determination condition last time" and "the end point is a time point thirty seconds before the execution time point of the instruction that has satisfied the determination condition this time". In other words, the criteria can be set to determine a time point predetermined time period away from the execution time point of the instruction that has satisfied the determination condition last time or the instruction that has satisfied the determination condition this time, as the start point or the end point. Alternatively, the criteria can be set in such a manner that "the start point is the time point thirty seconds before the execution time point of the instruction that has satisfied the determination condition this time" and "the end point is a time point thirty seconds after the execution time point of the instruction that has satisfied the determination condition this time".

In other words, both the criteria determining the start point and the end point can be set based on only the execution time point of the instruction that has satisfied the determination condition this time. The criteria of the start point and the end point of the grouping time period have been described assuming that they are set in advance in the above description, but can be provided to be changeable by the user as appropriate.

The end point may be unable to be acquired and the next start point may be inappropriately acquired after the start point is acquired, depending on the set criteria of the start point and the end point. Even in this case, no issue arises because only the time period chronologically surrounded by the start point and the end point is determined to be the grouping time period. This means that, when there is a time period in which the start point has come again after the start point, the display content during this time period is not contained in any group, and therefore the representative information is not generated either. As a result, the representative information can be prevented from being generated regarding, for example, a display content displayed only for an extremely short time period.

In step S240, based on the reproduction information of the group generated in step S230, the representative information generation unit 44 generates the representative information of this group. Then, the representative information generation unit 44 outputs the generated representative information to the second display control unit 45. First, the representative information generation unit 44 identifies the representative display content of this group according to a predetermined criterion from the reproduction information contained in this group. For example, the criterion is set so as to "select the display content displayed for the longest time period as the representative display content". If complying with this criterion, in the present step, the representative information generation unit 44 acquires each of the display time periods of the individual display contents from all of the pieces of reproduction information contained in this group, and identifies the display content having the longest display time period. In other words, the third acquisition unit acquires the representative information based on time periods during which the plurality of pieces of medical information contained in the group is displayed on the display unit. More specifically, the third acquisition unit acquires the above-described medical information displayed on the display unit for a longest time period among the plurality of pieces of medical information contained in the group as the representative information.

The criterion for identifying the representative display content described here is an example and is not seen to be limiting. For example, the criterion can be set to "select a display content at a middle time point of the grouping time period as the representative display content".

If each of the display contents is acquired as the image, the criterion can be set based on information indicating a feature amount of the image that is calculated using a known technique (hereinafter referred to as an image feature amount). For example, the medical information processing apparatus 10 can be configured to select an image including a maximum predetermined image feature amount (reproduction information including this image). In any case, any criterion can be set as long as the user can recognize a main point of this group from the representative display content.

Next, the representative information generation unit 44 acquires the display information data or the capture data from the reproduction information of the identified representative display content, and generates the representative information (the representative image in the present exemplary embodiment) from the acquired display information data or capture image. In the case where the acquired information is the display information data, the representative information generation unit 44 reproduces the display content from this display information data, and sets an image indicating the reproduced display content as the representative image. In the case where the acquired information is the capture image, the representative information generation unit 44 sets the capture image itself as the representative image. The representative information generation unit 44 can generate a second representative image by processing this representative image using a known technique, and utilize the second representative image in steps subsequent thereto. The second representative image refers to an image subjected to, for example, conversion processing that converts a tone, the enlargement ratio, the degree of transparency, or the like, and/or filter processing using a smoothing filter, a sharpening filter, or the like on the representative image. The icon or the mark simplifying the representative image can be set as the second representative image. The processing method for generating the second representative image can be determined in advance or can be specified by the user as appropriate. The presently described methods for generating the representative image and the second representative image described are merely examples and are not seen to be limiting.

In step S250, the second display control unit 45 controls displaying the representative information generated in step S240 on the display unit 36. If other representative information is already displayed in a region of the display unit 36 where the representative information is supposed to be displayed at this time, the second display control unit 45 displays this plurality of pieces of representative information while arranging them in a chronological order. Displaying the pieces of representative information of the individual groups while arranging them in the chronological order enables the user to view a history of work processes performed until that time.

In step S260, the control unit 37 determines whether an instruction to end the diagnostic imaging is issued from the user via the operation unit 35. The instruction to end the diagnostic imaging is issued by, for example, a selection of a button for ending the diagnostic imaging by the user. In a case where the instruction to end the diagnostic imaging is issued (YES in step S260), the processing ends. In a case where the instruction to end the diagnostic imaging is not issued (NO in step S260), the processing returns to step S200, and the processing ends in a case where the instruction is issued (YES in step S206).

Next, the processing procedure from steps S200 to S260 will be described with reference to FIGS. 3 to 8.

Figure 4A:
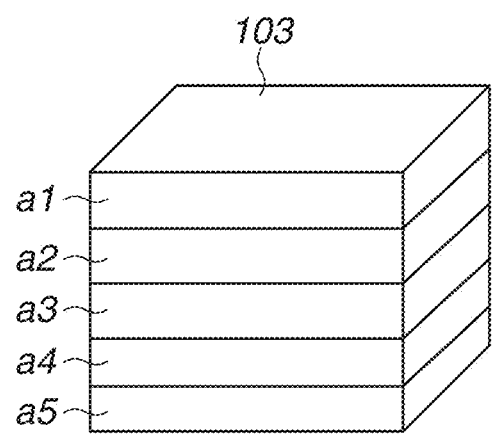
FIGS. 4A and 4B are diagrams each illustrating an example of a medical image.

First, suppose that, in step S200, the user issues an instruction "display a medical image 103". At this time, the first display control unit 40 reads out the medical image 103 of one patient from the database 22 to a medical image display device (a viewer) and displays the read medical image 103 on the display unit 36 based on the user's instruction. The medical image 103 exemplified in FIG. 3 is a horizontal cross section of a three-dimensional computed tomography (CT) image captured by a CT device, and is formed from five slice images a1 to a5 as illustrated in FIG. 4A. FIG. 3 illustrates a screen example on the display unit 36 immediately after processing corresponding to the present instruction is performed. In FIG. 3, a region 101 indicates a medical image display region. The medical image display region 101 is a region where a medical image targeted by the user for radiological interpretation or a medical image usable as reference information for the radiological interpretation is displayed. Displaying the medical image in the medical image display region 101 enables the user to use various functions of the medical image display device with respect to the displayed medical image. The user carries out the diagnostic imaging while sequentially changing the display content of the medical image displayed in the medical image display region 101 (by issuing an instruction) by utilizing these various functions. A region 102 indicates a representative information display region. The representative information display region 102 is a region where the representative information generated by the representative information generation unit 44 is displayed. In FIG. 3, the slice image a1 of the medical image 103 is displayed in the medical image display region 101. If the user issues an instruction to carry out a function regarding the change in the display content in step S200 at this time, the processing proceeds to step S210. In the present exemplary embodiment, since the user issues the instruction "display the medical image 103" at this time, the processing proceeds to step S210.

In step S210, the display content storage unit 42 acquires the display content on the display unit 36 at a time point immediately before a time point at which the user has issued the instruction "display the medical image 103", and stores the reproduction information thereof into the storage unit 34. The occasion at which the reproduction information is acquired and stored that is presently described is an example and is not seen to be limiting. For example, the reproduction information can be sequentially acquired and stored at a predetermined interval regardless of the user's instruction. In the present exemplary embodiment, assume that the reproduction information is the capture image and the display time period of the medical information with respect to which the instruction has been issued in the display state immediately before the processing corresponding to this instruction has been performed. However, the medical information with respect to which the instruction has been issued had not been displayed on the display unit 36 at the time point immediately before the time point at which the user has issued the instruction "display the medical image 103". In this manner, in the case where the target for the acquisition of the reproduction information does not exist, the processing in the present step is not performed. The processing in steps S210 to S250 is not performed either. In this manner, the processing in steps S210 to S250 is often unperformed when the user issues the instruction for the first time at the time of the diagnostic imaging. Therefore, the medical information processing apparatus 10 can be configured to skip the processing in steps S210 to S250 and cause the processing to proceed to step S260 when the user issues the instruction for the first time. In the present exemplary embodiment, the processing in steps S210 to S250 is also skipped, and the processing also proceeds to step S260. Then, in a case where the user does not issue the instruction to end the diagnostic imaging in step S260 (NO in step S260), the processing returns to step S200.

Suppose that, after the processing returns to step S200, the user next issues the instruction "carry out the function of advancing to the next slice" with respect to the medical image 103. At this time, the first display control unit 40 changes the displayed slice image from a1 to a2. After processing according to the present instruction is performed, the slice image a2 of the medical image 103 is displayed in the medical image display region 101. Since the instruction to change the display content is acquired at this time, the processing proceeds to step S210.

In step S210, the display content storage unit 42 acquires the display content on the display unit 36 at a time point immediately before a time point at which the user has issued the instruction "carry out the function of advancing to the next slice", and stores the reproduction information thereof in the storage unit 34. In other words, the display content storage unit 42 acquires and stores the capture image and the display time period of the medical information with respect to which the instruction has been issued in the display state immediately before the processing corresponding to the present instruction has been performed. The system, for example, automatically measures a time period elapsed since a time point at which an instruction has been issued last time until a time point at which an instruction has been issued this time, by which the display time period can be acquired. In the present exemplary embodiment, the display content storage unit 42 acquires and stores a capture image of the slice image a1 and a display time period of the slice image a1 (assumed to be one second) as the reproduction information.

In step S220, the user instruction determination unit 41 determines whether the user's instruction "carry out the function of advancing to the next slice" satisfies the determination condition. In the present exemplary embodiment, suppose that two conditions "the determination target instruction is the instruction to change the observation target" and "the determination target instruction is the instruction to carry out the density conversion function" are set as the determination conditions. The user's instruction "carry out the function of advancing to the next slice" does not satisfy any of these determination conditions (NO in step S220). Therefore, the processing returns to step S200.

Suppose that, after the processing returns to step S200, the user issues the instruction "carry out the function of advancing to the next slice" with respect to the medical image 103 again. At this time, the first display control unit 40 changes the displayed slice image from a2 to a3. Since the instruction to change the display content is provided at this time, the processing proceeds to step S210. In step S210, the display content storage unit 42 acquires and stores a capture image of the slice image a2 and a display time period of the slice image a2 (assumed to be three seconds) as the reproduction information, similarly to the above-described step. Since this instruction does not satisfy the determination conditions in step S220 (NO in step S220), the processing returns to step S200.

Figure 4B:
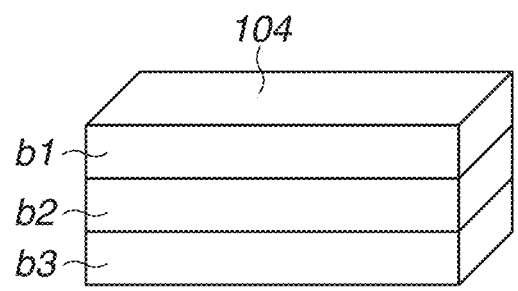

Suppose that, after the processing returns to step S200, the user next issues an instruction "change the observation target to a medical image 104". At this time, the first display control unit 40 reads out another medical image 104 of the same patient from the database 22 and displays the read medical image 104 on the display unit 36, thereby changing the observation target to the medical image 104. The medical image 104 is a coronal cross section of the three-dimensional CT image captured by the CT device, and is formed from three slice images b1 to b3 as illustrated in FIG. 4B. After processing corresponding to the present instruction is performed, the slice image b1 of the medical image 104 is displayed in the medical image display region 101. Since the instruction to change the display content is provided at this time, the processing proceeds to step S210.

In step S210, the display content storage unit 42 acquires the display content on the display unit 36 at a time point immediately before a time point at which the user has issued the instruction "change the observation target to the medical image 104", and stores the reproduction information thereof into the storage unit 34. More specifically, the display content storage unit 42 acquires and stores a capture image of the slice image a3 and a display time period of the slice image a3 (assumed to be two seconds) as the reproduction information.

In step S220, the user instruction determination unit 41 determines whether the user's instruction "change the observation target to the medical image 104" satisfies the determination conditions. The determination conditions in the present exemplary embodiment include the condition "the determination target instruction is the instruction to change the observation target" as described above, and the user's instruction "change the observation target to the medical image 104" satisfies this determination condition (YES in step S220). Therefore, the processing proceeds to step S230. FIG. 5 illustrates how the pieces of reproduction image stored since the start of the diagnostic imaging until the end of the present step look like. In FIG. 5, the user's instruction and the reproduction information stored based on this instruction are indicated in a chronological order from a top to a bottom of the drawing. A left column in the drawing illustrates a schematic diagram of the stored capture image and a right column indicates the display time period corresponding thereto. Hereinafter, reproduction information formed from a pair of the capture image of the slice image a1 and the display time period corresponding thereto (one second) will be referred to as $\inf_{200}$. Similarly, reproduction information formed from a pair of the capture image of the slice image a2 and the display time period corresponding thereto (three seconds) will be referred to as $\inf_{210}$, and reproduction information formed from a pair of the capture image of the slice image a3 and the display time period corresponding thereto (two seconds) will be referred to as $\inf_{220}$.

In step S230, the group generation unit 43 reads out the pieces of reproduction information stored during the predetermined time period from the display content storage unit 42, and groups them. In the present exemplary embodiment, suppose that the criterion "the execution time point of the instruction that has satisfied the determination condition last time" or "an execution time point of an instruction that has been issued for the first time" is set as the criterion for determining the start point of the grouping time period. Suppose that the criterion "the time point immediately before the execution time point of the instruction that has satisfied the determination condition this time" is set as the criterion for determining the end point of the grouping time period. In other words, the grouping time period is set to a time period since the "execution time point of the instruction to display the medical image 103" until the "time point immediately before the execution time point of the instruction to change the observation target to the medical image 104". Therefore, the group generation unit 43 groups the three pieces of reproduction information $\inf_{200}$, $\inf_{210}$, and $\inf_{220}$ as one group, as the reproduction information of this grouping time period.

In step S240, the representative information generation unit 44 identifies the representative display content (the representative information) of the group generated in step S230. In the present exemplary embodiment, suppose that the criterion "select the display content displayed for the longest time period as the representative display content" is set as the criterion for identifying the representative display content. The representative display content, however, may be unable to be identified based on this criterion, like when there is a plurality of display contents displayed for equal time periods. In preparation for such a case, in the present exemplary embodiment, suppose that a criterion "select a display content close to the middle time point in the grouping time period from the display contents identified based on this criterion" is set as a second criterion. In other words, the medical information processing apparatus 10 is configured to be able to identify the representative display content by combining a plurality of criteria. In the example illustrated in FIG. 5, the representative information generation unit 44 compares the display time periods in the three pieces of reproduction information $inf_{200}$, $inf_{210}$, and $inf_{220}$ to identify the representative display content. In the case of the present exemplary embodiment, the display time period in $inf_{210}$ is three seconds and is longest, and therefore the display content corresponding to $inf_{210}$ is selected as the representative display content. Next, the representative information generation unit 44 acquires the capture image of the display content from $inf_{210}$ (the capture image of the slice image a2 in this case). Then, the representative information generation unit 44 converts this capture image into a size suitable to be displayed in the representative information display region 102. The capture image after the conversion processing will be referred to as a representative image 300.

In step S250, the second display control unit 45 displays the representative image 300 generated in step S240 on the display unit 36. FIG. 6 illustrates a screen example displayed on the display unit 36 after the present step. In the example illustrated in FIG. 6, the slice image a3 of the medical image 103 and the slice image b1 of the medical image 104 are displayed in the medical image display region 101. The representative image 300 is displayed in the representative information display region 102.

In a case where the user does not issue the instruction to end the diagnostic imaging in step S260 (NO in step S260), the processing returns to step S200. Suppose that, after the processing returns to step S200, the user next issues the instruction "carry out the function of advancing to the next slice" with respect to the medical image 104. At this time, the first display control unit 40 changes the displayed slice image from b1 to b2. Since the instruction to change the display content is acquired at this time, the processing proceeds to step S210. In the steps subsequent thereto, in step S210, the display content storage unit 42 acquires and stores a capture image of the slice image b1 and a display time period of the slice image b1 (assumed to be two seconds) as the reproduction information, similarly to the above-described step. Since the present instruction does not satisfy the determination conditions in step S220 (NO in step S220), the processing returns to step S200.

Suppose that, after the processing returns to step S200, the user issues the instruction "carry out the density conversion function" with respect to the medical image 104. At this time, the first display control unit 40 converts a pixel value that each of pixels in the medical image 104 has when being displayed. Since the instruction to change the display content is provided at this time, the processing proceeds to step S210.

In step S210, the display content storage unit 42 acquires the display content on the display unit 36 at a time point when the user has issued the instruction "carry out the density conversion function", and stores the reproduction information thereof in the storage unit 34. More specifically, the display content storage unit 42 acquires and stores a capture image of the slice image b2 and a display time period of the slice image b2 (assumed to be six seconds) as the reproduction information.

In step S220, the user instruction determination unit 41 determines whether the user's instruction "carry out the density conversion function" satisfies the determination conditions. The determination conditions in the present exemplary embodiment include the condition "the determination target instruction is the instruction to carry out the density conversion function" as described above, and the instruction "carry out the density conversion function" satisfies this determination condition (YES in step S220). Therefore, the processing proceeds to step S230. FIG. 7 illustrates how the pieces of reproduction information stored since the start of the diagnostic imaging until the end of the present step appear. In FIG. 7, the user's instruction and the reproduction information stored based on this instruction are indicated in the chronological order from a top to a bottom of the drawing, similarly to FIG. 5. Hereinafter, reproduction information formed from a pair of the capture image of the slice image b1 and the display time period corresponding thereto (two seconds) will be referred to as $inf_{230}$. Similarly, reproduction information formed from a pair of the capture image of the slice image b2 and the display time period corresponding thereto (six seconds) will be referred to as $inf_{240}$.

In step S230, the group generation unit 43 reads out the pieces of reproduction information stored during the grouping time period, and groups them. In the present exemplary embodiment, the start point and the end point of the grouping time period are set to the "execution time point of the instruction that has satisfied the determination condition last time", and the "time point immediately before the execution time point of the instruction that has satisfied the determination condition this time", respectively, based on the above-described criteria. In other words, the grouping time period is set to a time period since the "execution time point of the instruction to change the observation target to the medical image 104" until the "time point immediately before the execution time point of the instruction to carry out the density conversion function". Therefore, the group generation unit 43 groups the two pieces of reproduction information $inf_{230}$ and $inf_{240}$ as one group, as the reproduction information of this grouping time period.

In step S240, the representative information generation unit 44 identifies the representative display content of the new group, and generates the representative image. In the present exemplary embodiment, the representative information generation unit 44 compares the display time periods in the two pieces of reproduction information $inf_{230}$ and $inf_{240}$ based on the above-described condition. The display time period in $inf_{240}$ is six seconds and is longest, and therefore the display content corresponding to $inf_{240}$ is selected as the representative display content. Next, the representative information generation unit 44 acquires the capture image of this display content (the capture image of the slice image b2 in this case) from $inf_{240}$. Then, the representative information generation unit 44 converts this capture image into a size displayable in the representative information display region 102. The representative information generation unit 44 sets the capture image after the conversion processing as a representative image 310. The size of the representative image in the present conversion processing is adjusted to the same size as the representative image 300 already displayed in the representative information display region 102.

In step S250, the second display control unit 45 displays the representative image 310 generated in step S240 on the display unit 36. At this time, the representative image 300 is already displayed in the representative information display region 102 on the display unit 36. Therefore, the representative image 310 is displayed while being arranged together with the representative image 300 in the chronological order. FIG. 8 illustrates a screen example on the display unit 36 after the present step. The slice image a3 of the medical image 103 and the slice image b2 after the medical image 104 is subjected to the density conversion are displayed in the medical image display region 101. The representative image 300 and the representative image 310 are displayed in the representative information display region 102 while being arranged in the chronological order from a left side to a right side of the drawing.

In step S260, the user issues the instruction to end the diagnostic imaging. Therefore, the processing in the present exemplary embodiment ends.

The medical information processing apparatus 10 according to the present exemplary embodiment includes at least the following advantageous effects. The main point of each of the work processes is displayed in chronological order even in diagnostic imaging requiring complicated work processes so that the user can easily and correctly confirm an execution status and an execution order (an execution history) of each of the work processes. Therefore, the present exemplary embodiment provides a medical information processing apparatus and a medical information processing method that prevents reduction in quality and efficiency of the user's diagnostic imaging.

In the present exemplary embodiment, the processing in steps S240 and S250 is performed with respect to all of the groups generated in step S230, and the representative images of all of the groups are displayed. However, the displayed representative images can be the representative images of a part of the groups.

In this case, the representative information generation unit 44 can determine whether to perform the processing in steps S240 and 250 based on the reproduction information of the group generated in step S230. In this case, the representative information generation unit 44 can achieve the intended result by performing processing for determining whether the generated group satisfies a group selection condition, and changing the processing procedure based on a result of the determination at a time point between step S230 and step S240 (step S231). More specifically, the medical information processing apparatus can achieve the intended result by causing the processing to proceed to step S240 in a case where the group satisfies the group selection condition while returning to step S200 in a case where the group does not satisfy the group selection condition.

Figure 9:
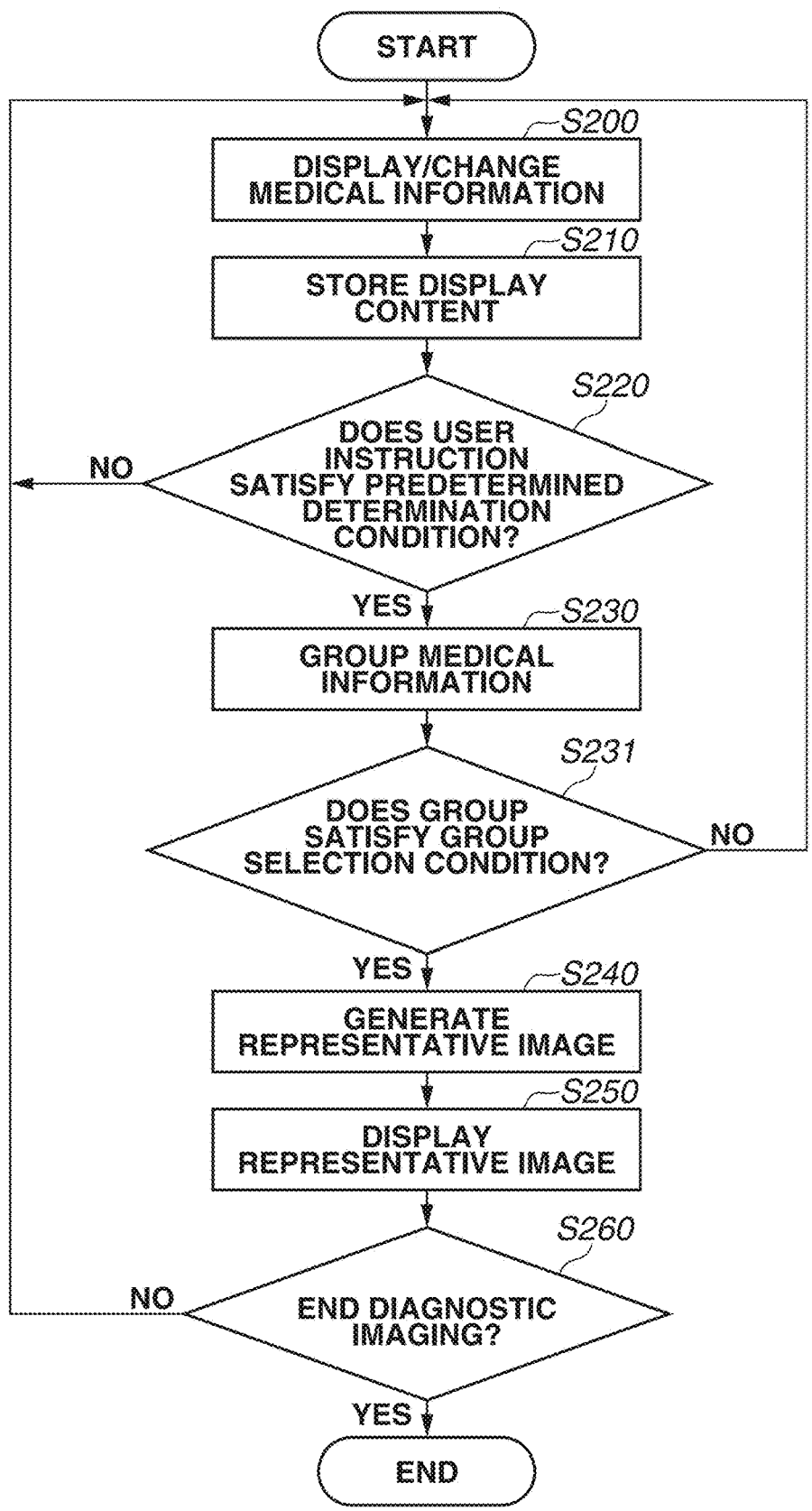
FIG. 9 is a flowchart illustrating an example of overall processing according to an exemplary modification 1-1.

FIG. 9 illustrates a flowchart of an exemplary modification (an exemplary modification 1-1) of the above-described exemplary embodiment. Compared to FIG. 2, FIG. 9 is different therefrom in terms of the addition of step S231, which is the processing for determining the group, after step S230. The group selection condition refers to a condition for determining whether to generate and display the representative image of this group, and is assumed to be set in advance. More specifically, the group selection condition is, for example, a condition "the number of pieces of reproduction information contained in the group is five or more" or a condition "a maximum number among the display time periods in all of the pieces of reproduction information contained in the group is one second or longer". In other words, the third acquisition unit does not acquire the representative information if the number of pieces of medical information contained in the group is a threshold value or smaller. The third acquisition unit can be configured to not output the representative information acquired from the group in which the number of pieces of medical information contained in the group is a threshold value or smaller to the display unit.

The group selection condition described here is a mere example and is not seen to be limiting as long as a group necessary for the user to understand the main point of the diagnostic imaging can be selected. In the above description, the group selection condition is described assuming that the group selection condition is set in advance, but can be provided to be changeable by the user as appropriate.

As another method, the representative information generation unit 44 can determine whether to perform the processing in step S250, based on the representative image generated in step S240. In this case, the representative information generation unit 44 can achieve the intended result by performing processing for determining whether the representative image satisfies a representative image selection condition and changing the processing procedure based on a result of the determination at a time point between step S240 and step S250 (step S241). More specifically, the medical information processing apparatus can achieve the intended result by causing the processing to proceed to step S250 if the representative image satisfies the representative image selection condition while returning to step S200 if the representative image does not satisfy the representative image selection condition.

Figure 10:
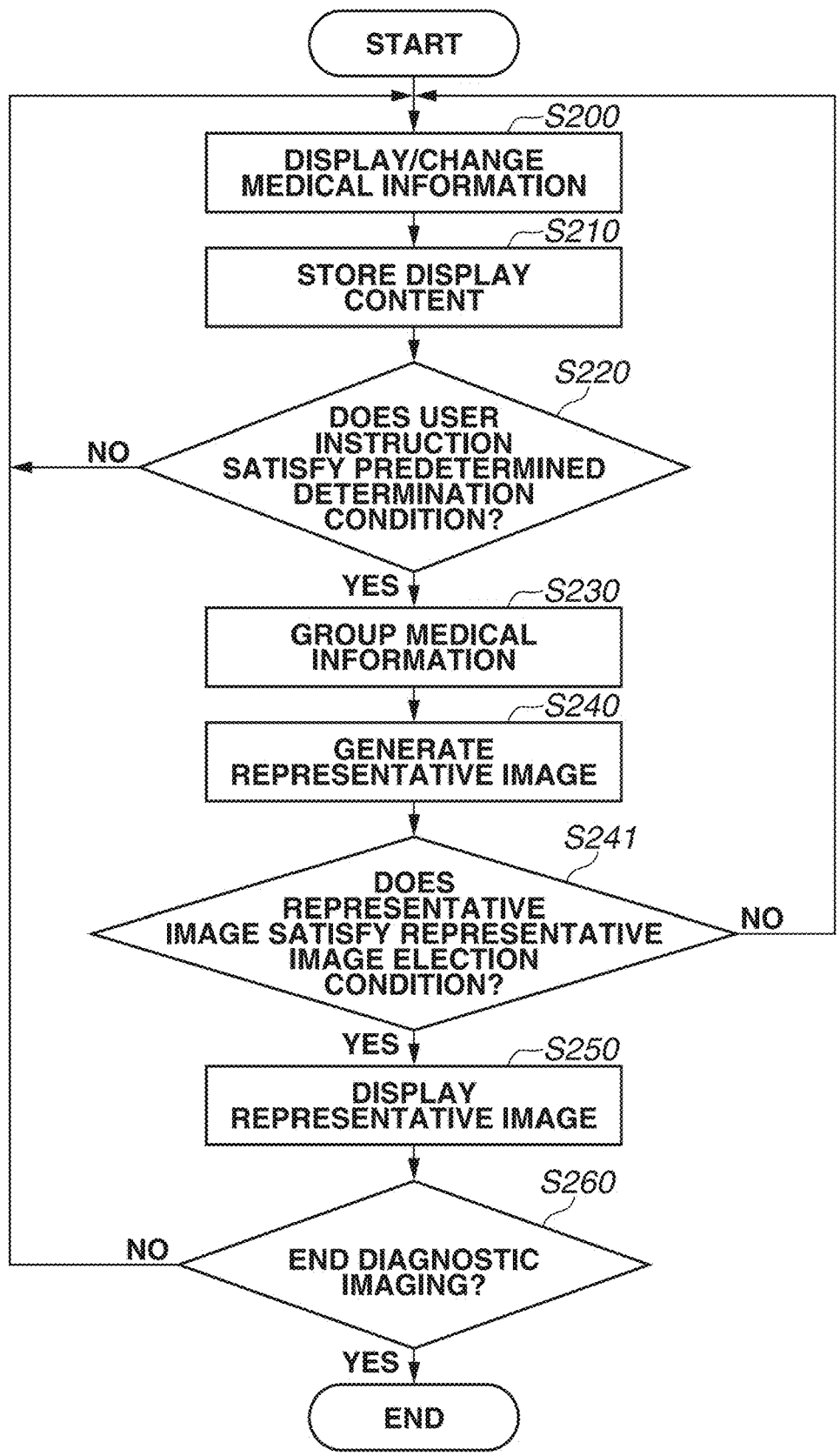
FIG. 10 is a flowchart illustrating an example of overall processing according to an exemplary modification 1-2.

FIG. 10 illustrates a flowchart of another exemplary modification (an exemplary modification 1-2) of the above-described exemplary embodiment. Compared to FIG. 2, FIG. 10 is different therefrom in terms of the addition of step S241, which is the processing for determining the representative image, after step S240. The representative image selection condition refers to a condition for determining whether to display this representative image, and is assumed to be set in advance. More specifically, the representative image selection condition is, for example, a condition "the number of pixels is 10000 or more" or a condition "a percentage of the number of pixels having a pixel value of 0 or smaller among all pixels is fifty percent or lower". The representative image selection condition described here is a mere example and is not seen to be limiting as long as the representative image necessary for the user to understand the main point of the diagnostic imaging can be selected. For example, the representative image selection condition can be set based on the image feature amount that can be calculated using a known technique. In the above description, the representative image selection condition is described assuming that the representative image selection condition is set in advance, but can be provided to be changeable by the user as appropriate.

Figure 11:
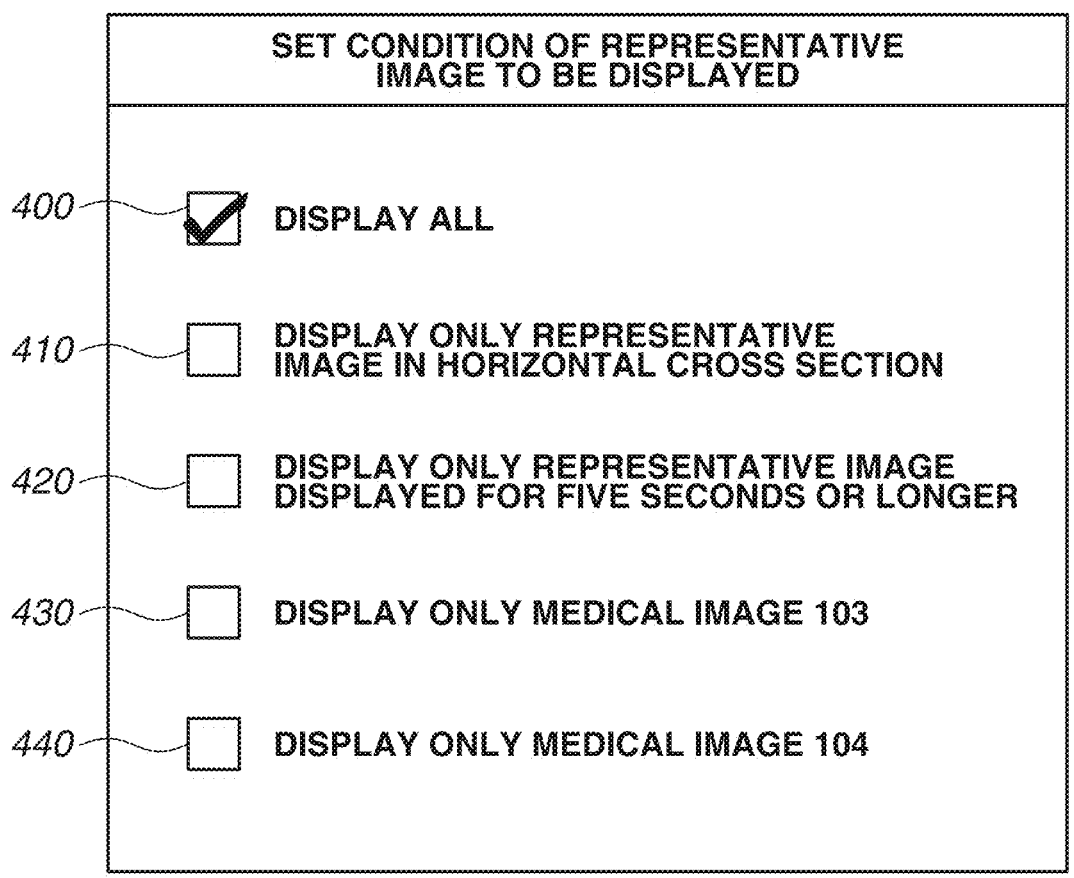
FIG. 11 illustrates an example of a screen where a display condition is set.

The representative image displayed in step S250 can be changed based on the user's instruction as appropriate. This configuration can be realized by, for example, presenting a screen where a condition of the representative image to be displayed (hereinafter referred to as a display condition) is set to the user like an example illustrated in FIG. 11, and prompting the user to select this condition. FIG. 11 illustrates an example presenting five display conditions 400 to 440, and, at each of the conditions, a check box and an explanatory text of the condition are presented as a pair. The user selects at least one from the respective check boxes. FIG. 11 illustrates an example where the display condition 400 is selected. Then, the intended configuration can be realized by controlling the display to display only the representative image satisfying the condition corresponding to the checked box. The display condition described here is a mere example and is not seen to be limiting. The medical information processing apparatus 10 can automatically adjust a display interval between the individual representative images in the representative information display region 102 when switching the representative image to be displayed.

By implementing the present exemplary modification, the medical information processing apparatus can select the group and the representative image necessary for the user to understand the main point of the diagnostic imaging, and display only the necessary representative image. Therefore, the user can further easily and correctly confirm the execution status and the execution order of each of the work processes in the diagnostic imaging task.

In the description mentioned above, the size of the representative image generated in step S240 when and after the processing is performed for the second time is determined based on the size of the already displayed representative image. However, the method for determining the size of the representative image is not seen to be limiting For example, the size of the representative image can be determined based on the reproduction information corresponding to the representative image. In the following description, the determination method in a case where the size of the representative image is determined based on the display time period in the reproduction information will be described.

In FIG. 7, the display time period in $\inf_{210}$ is three seconds, and the display time period in $\inf_{240}$ is six seconds. The size of the representative image is determined based on a difference between these display time periods. More specifically, the display time period in $\inf_{240}$ is twice the display time period in $\inf_{210}$, and therefore the size of the representative image 310 can be determined to be twice the representative image 300. Alternatively, only a size of the representative image in a horizontal direction (or only a size in a vertical direction) can be determined to be twice in consideration of a shape of the representative information display region 102. The size can be determined based on a value acquired by multiplying a ratio of the display time period by an arbitrary constant.

Figure 12:
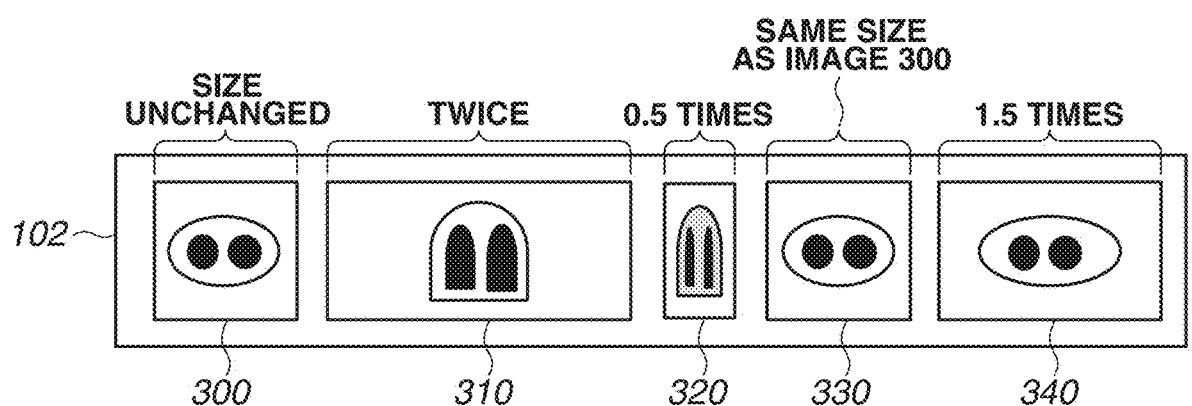
FIG. 12 illustrates a screen example of a representative image display region according to an exemplary modification 2.

FIG. 12 illustrates a screen example of the representative information display region 102 when only the size of the representative image in the horizontal direction is determined based on the difference in the display time period according to another exemplary modification (exemplary modification 2). In FIG. 12, the representative image 300, the representative image 310, a representative image 320, a representative image 330, and a representative image 340 are displayed in the representative information display region 102. Suppose that the display time period in the reproduction information corresponding to the representative image 300 is three seconds. Similarly, suppose that the representative image 310, the representative image 320, the representative image 330, and the representative image 340 are six seconds, 1.5 seconds, three seconds, and 4.5 seconds, respectively. The size of each of the representative images in the horizontal direction is determined based on the difference in the display time period from the representative image 300, and the representative images are displayed accordingly.

More specifically, the representative image 310 is displayed in a size twice the representative image 300 in the horizontal direction. The representative image 320 is displayed in a size 0.5 times the representative image 300 in the horizontal direction. The representative image 330 is displayed in the same size as the representative image 300 in the horizontal direction. The representative image 340 is displayed in a size 1.5 times the representative image 300 in the horizontal direction. The method for determining the size of the representative image described in the present exemplary modification is a mere example, and this determination method can be any method as long as the size of the representative image is determined based on the reproduction information. For example, the size of the representative image can be determined based on the number of pieces of reproduction information in the group, or can be determined based on a sum of the display time periods in the pieces of reproduction information in the group. Alternatively, the size of the representative image can be determined based on a difference in the number of times that the representative image is displayed, or can be determined based on the image feature amount of each of the display contents that can be calculated using a known technique. The medical information processing apparatus 10 can be configured to enable the user to switch the method for determining the size of the representative image as appropriate. This configuration can be realized by switching the display as appropriate based on, for example, a selection of a switching button (not illustrated).

Implementing the present exemplary modification enables the user to understand a part of a characteristic of each of the representative images from the size of the representative image. Therefore, the user can easily confirm the execution status and the execution order of each of the work processes in the diagnostic imaging task.

The present exemplary embodiment has been described referring to the example in which the number of displayed representative images (hereinafter referred to as the number of representative images) is small (the number of representative images in the present exemplary embodiment is two). In a case where the number of representative images is large, it may be impossible to display all of the representative images in the representative information display region 102. In the following description, a handling method in the case where the number of representative images is large will be described.

As a first method, the large number of representative images can be handled by changing the size of the representative information display region 102 based on the number of representative images. More specifically, the large number of representative images can be handled by calculating a size of a region that displays all of the representative images from a sum of the sizes of all of the representative images to be displayed, and changing the size of the representative information display region 102 to the calculated size.

As a second method, the large number of representative images can be handled by changing the size of each of the representative images based on the number of representative images. More specifically, the large number of representative images can be handled by dividing the size of the representative information display region 102 by the number of representative images to thereby calculate a size enabling all of the representative images to be displayed in the representative information display region 102, and changing the sizes of the representative images to the calculated size.

As a third method, the large number of representative images can be handled by keeping the size of the representative information display region 102 and the sizes of the representative images constant, and selecting the representative images corresponding to the number of representative images based on a predetermined condition. This condition is set to, for example, a condition "select the representative images in an order of time points at which the representative images are generated from latest to earliest". This method will be specifically described with reference to FIGS. 13A to 13C, which illustrate a screen example of a representative image display region according to yet another exemplary modification (exemplary modification 3).

Figure 13A:
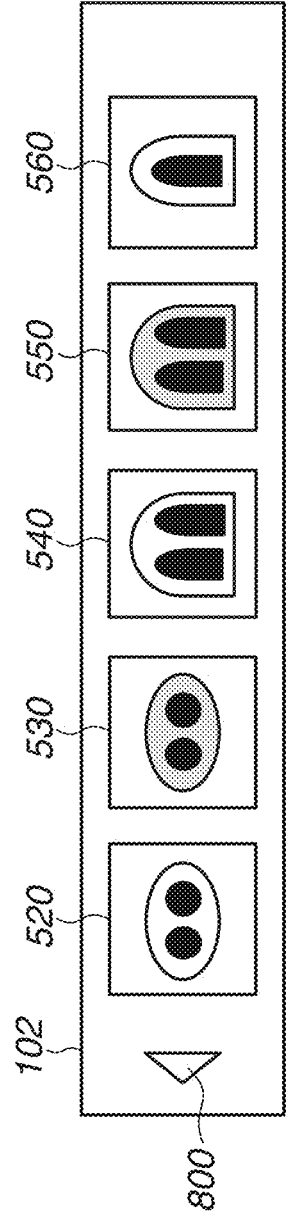
FIGS. 13A to 13C are diagrams each illustrating a screen example of a representative image display region according to an exemplary modification 3.
Figure 13B:
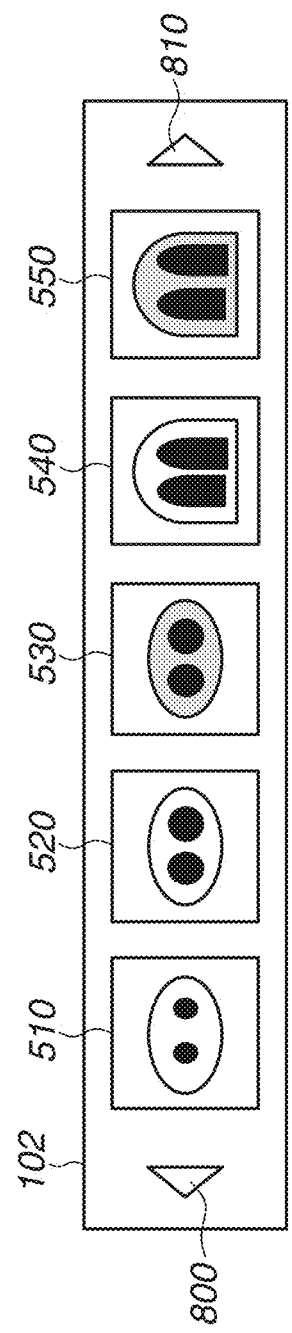
Figure 13C:
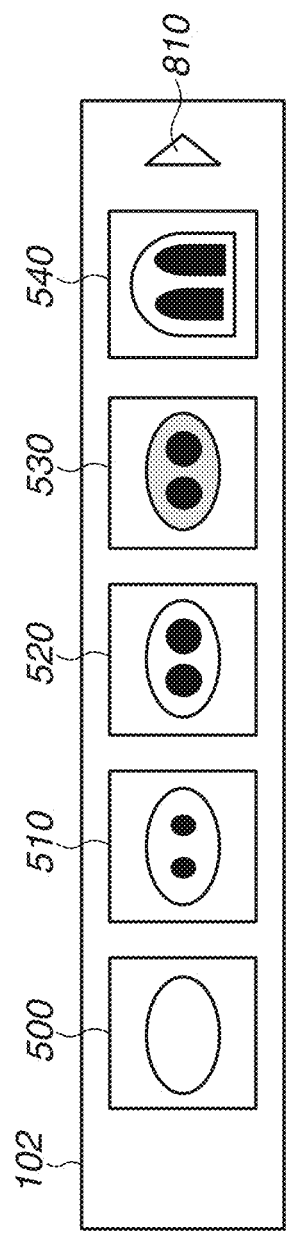

Suppose that the number of representative images in FIGS. 13A to 13C is five, and time points at which they are generated are old in an order of representative images 500 to 560. In other words, suppose that the representative image 500 is generated at the earliest time point, and the representative image 560 is generated at the latest time point. Under the above-described condition, the representative image 560, the representative image 550, the representative image 540, the representative image 530, and the representative image 520 are selected as the representative images to be displayed in the representative information display region 102 to be displayed. Then, the selected representative images are displayed in the chronological order. FIG. 13A illustrates a screen example of the display screen 36 after the present processing. The representative images 520 to 560 are displayed in the chronological order from a left side to a right side of the drawing. The medical information processing apparatus 10 can be configured to enable the user to appropriately change the time points at which the representative images to be displayed have been generated.

A button 800 and a button 810 illustrated in FIGS. 13A to 13C are buttons for changing the time points at which the representative images to be displayed have been generated. The user can change the time points at which the representative images to be displayed have been generated by selecting the button 800 or the button 810. For example, when the user selects the button 800, a representative image generated at the latest time point (the representative image 560 in FIG. 13A) among the displayed representative images is deleted from the screen. Then, the latest representative image (the representative image 510 in FIGS. 13A to 13C), which is the one among representative images generated at earlier time points than a representative image generated at the earliest time point (the representative image 520 in FIG. 13A) among the displayed representative images, is displayed.

FIG. 13B illustrates a screen example when the user selects the button 800 from the state illustrated in FIG. 13A. Comparing FIG. 13B to FIG. 13A, the representative image 560 is deleted and the representative image 510 is displayed, and the representative images 520 to 550 are displayed in the chronological order. Similarly, FIG. 13C illustrates a screen example when the user selects the button 800 again from the state of the screen example illustrated in FIG. 13B. When the user selects the button 810, a representative image generated at the earliest time point (the representative image 500 in FIG. 13C) among the displayed representative images is deleted from the screen. Then, the earliest representative image (the representative image 550 in FIGS. 13A to 13C), which is the one among representative images generated at later time points than a representative image generated at the latest time point (the representative image 540 in FIG. 13C) among the displayed representative images, is displayed. In other words, when the user selects the button 810 from the state illustrated in FIG. 13C, the screen transitions to the state illustrated in FIG. 13B. Similarly, when the user selects the button 810 from the state illustrated in FIG. 13B, the screen transitions to the state illustrated in FIG. 13A.

In the present exemplary embodiment, the time points at which the representative images to be displayed have been generated are changed based on the selection of the button, but can be changed based on, for example, a mouse wheel operation on the mouse or a flick operation on a touch panel display. The condition for selecting the representative images described as the third method is a mere example and is not seen to be limiting. For example, this condition can be set to a condition "select the representative images in descending order of the display time period in the reproduction information corresponding to each of the representative images". The large number of representative images can be handled by selecting the representative images as many as a number not exceeding the number of representative images from the plurality of representative images using this condition and displaying only the selected representative images in the chronological order in this manner. In other words, the display unit displays the plurality of pieces of representative information while arranging them in a chronological order. Implementing the present exemplary modification enables the representative images to be displayed in the representative information display region 102 even when the number of representative images is large.

In the present exemplary embodiment, the condition for determining the user's instruction in step S220 is set based on only the content of the user's instruction. The present exemplary modification will be described as an example in which this determination condition is set based on both the content of the user's instruction and the image feature amount calculated from the image.

As a processing procedure according to the present exemplary modification, an image analysis unit (not illustrated) that can, for example, be included in the control unit 37 and realized by a processor, calculates the image feature amount of the image displayed in step S200 and outputs a result thereof to the user instruction determination unit 41 at a time point between step S200 and step S220. Then, in step S220, the user instruction determination unit 41 sequentially acquires both the user's instruction in step S200 and the image feature amount calculated from the image, and determines whether the user's instruction satisfies the determination condition based on both of them, by which the present exemplary modification can be realized.

Figure 14:
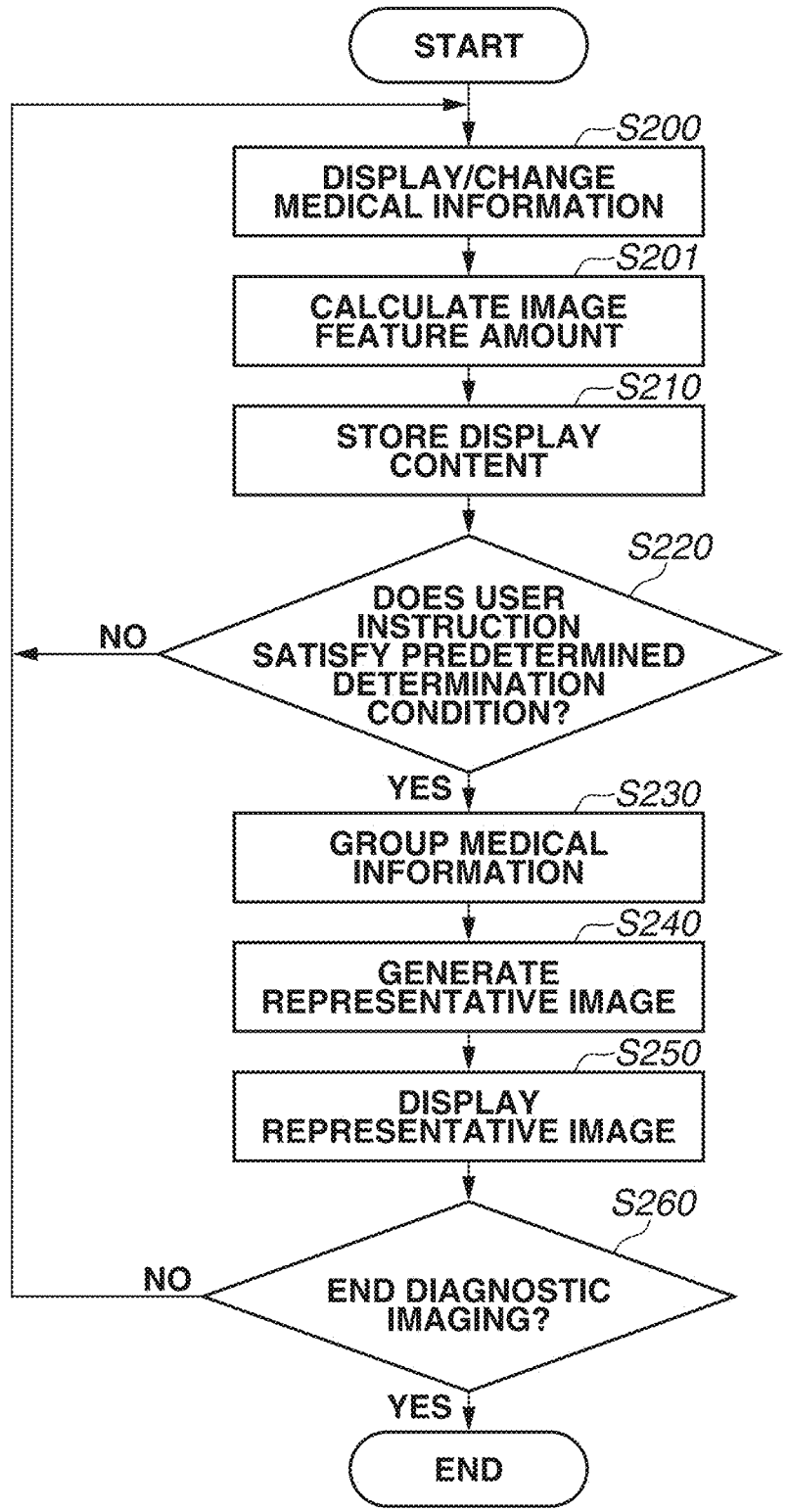
FIG. 14 is a flowchart illustrating an example of overall processing according to an exemplary modification 4.

FIG. 14 illustrates a flowchart at the time of another exemplary modification (exemplary modification 4). Compared to FIG. 2, FIG. 14 is different therefrom in terms of a new addition of step S201 for calculating the image feature amount after step S200. FIG. 14 illustrates the example in which step S201 is performed before step S210, but step S201 may be performed between step S210 and step S220.

The processing according to the present exemplary modification will be specifically described with reference to FIGS. 3 and 4. Suppose that the determination condition in the present example is as follows: satisfying both a first condition "the determination target instruction is the instruction to carry out the function of advancing to the next slice" and a second condition "organs imaged in respective slice images before and after the function of advancing to the next slice is carried out are different from each other".

Suppose that, in step S200, the user issues the instruction "display the medical image 103". At this time, the first display control unit 40 displays the slice image a1 of the medical image 103 on the display unit 36 according to the user's instruction. Since the instruction to change the display content can be acquired at this time, the processing proceeds to step S201.

In step S201, the image analysis unit (not illustrated) employs a known image processing technique with respect to the slice image a1 of the medical image 103 displayed in step S200 to identify an organ imaged in the slice image a1. In the present example, suppose that the organ imaged in the slice image a1 is identified as a "lung".

In step S210, the processing in steps S210 to S250 is not performed with respect to the instruction issued for the first time at the time of the diagnostic imaging in the present example, either. Therefore, the processing proceeds to step S260. Then, in a case where the user does not issue the instruction to end the diagnostic imaging in step S260 (NO in step S260), the processing returns to step S200.

Suppose that, after the processing returns to step S200, the user next issues the instruction "carry out the function of advancing to the next slice" with respect to the medical image 103. At this time, the first display control unit 40 changes the displayed slice image from a1 to a2. Since the instruction to change the display content is acquired at this time, the processing proceeds to step S201.

In step S201, the image analysis unit (not illustrated) performs similar processing on the slice image a2 of the medical image 103 displayed in step S200 to identify an imaged organ. In the present example, suppose that the organ imaged in the slice image a2 is identified as the "lung".

In step S210, the display content storage unit 42 acquires the display content on the display unit 36 at a time point immediately before a time point at which the instruction "carry out the function of advancing to the next slice" has been executed, and stores the reproduction information thereof into the storage unit 34.

In step S220, the user instruction determination unit 41 determines whether the user's instruction satisfies the above-described determination condition based on both the user's instruction "carry out the function of advancing to the next slice" and the image feature amount calculated in step S201. The determination target instruction is the instruction "carry out the function of advancing to the next slice" and therefore satisfies the first condition. The organ imaged in the image before the function of advancing to the next slice has been carried out (the slice image a1 in this case) is the "lung", and the organ imaged in the image after the function of advancing to the next slice has been carried out (the slice image a2 in this case) is also the "lung". In other words, the present user's instruction does not satisfy the second condition. Therefore, the processing returns to step S200.

Suppose that, after the processing returns to step S200, the user issues the instruction "carry out the function of advancing to the next slice" with respect to the medical image 103 again. At this time, the first display control unit 40 changes the displayed slice image from a2 to a3. Since the instruction to change the display content is acquired at this time, the processing proceeds to step S201.

In step S201, the image analysis unit performs similar processing on the slice image a3 of the medical image 103 displayed in step S200 to identify an imaged organ. In the present example, suppose that the organ imaged in the slice image a3 is identified as a "liver". In step S210, the display content storage unit 42 acquires the display content on the display unit 36 at a time point immediately before a time point at which the instruction "carry out the function of advancing to the next slice" has been executed, and stores the reproduction information thereof into the storage unit 34.

In step S220, the user instruction determination unit 41 determines whether the user's instruction satisfies the above-described determination condition. The determination target instruction is the instruction "carry out the function of advancing to the next slice" and therefore satisfies the first condition. The organ imaged in the image before the function of advancing to the next slice has been carried out (the slice image a2 in this case) is the "lung", and the organ imaged in the image after the function of advancing to the next slice has been carried out (the slice image a3 in this case) is the "liver". In other words, the present user's instruction satisfies the second condition. Therefore, the processing proceeds to step S230.

In other words, the group generation unit 43 groups the plurality of pieces of medical information acquired by the second acquisition unit based on the user's instruction acquired by the first acquisition unit and feature information of the medical information. More specifically, the feature information is information indicating a site of a subject that is contained in the medical information, and the group generation unit 43 groups the pieces of medical information if the site of the subject is changed in the sequentially displayed medical information. Step S240 and the steps subsequent thereto are similar to the present exemplary embodiment.

The determination condition described in the present exemplary modification is a mere example and is not seen to be limiting. Any determination condition can be set as long as the determination condition is set based on both the content of the user's instruction and the image feature amount. The medical information processing apparatus 10 can be configured to use only the determination criterion set based on only the image feature amount. The medical information processing apparatus 10 can be configured to estimate the information of the user's instruction based on the image feature amount of the display image without directly acquiring the information of the user's instruction from the operation unit 35.

For example, the medical information processing apparatus 10 can be configured to determine the "instruction to change the display image" and the "instruction to carry out the density conversion function" based on a change in a value of the display image (for example, a difference in an average pixel value). In this case, the image analysis unit corresponds to an example of a first acquisition unit configured to acquire an image feature amount of a medical image displayed on a display unit. The group generation unit 43 corresponds to an example of a group generation unit configured to group the plurality of medical images acquired by the second acquisition unit, based on the image feature amount acquired by the first acquisition unit.

In the present exemplary modification, the image feature amount is calculated every time the slice image displayed based on the user's instruction is changed. However, the image feature amounts of all of the slice images can be calculated after the image to be read out in step S200 is determined. In this case, this configuration can be realized by storing the calculated image feature amount in the storage unit 34 or the RAM 33 in association with the slice image in advance, and reading out the corresponding image feature amount to utilize it when displaying the slice image.

Implementing the present exemplary modification enables the medical information processing apparatus 10 to generate the group and display the representative image thereof in consideration of not only the content of the user's instruction, but also the content of the image. Therefore, the user can correctly confirm the execution status and the execution order (the execution history) of each of the work processes in the diagnostic imaging task.

In the present exemplary embodiment, the medical information processing apparatus 10 has been described as using one medical information display device, i.e., the medical image display device in the present exemplary embodiment. However, the medical information display device is not limited to the medical image display device, and the medical information processing apparatus 10 can also use a plurality of medical information display devices.

In the following description, an example in which the user engages in the diagnostic imaging task while displaying a plurality of types of medical information on the plurality of display devices will be specifically described with reference to FIGS. 15 to 18, which illustrate another exemplary modification (exemplary modification 5).

Figure 15:
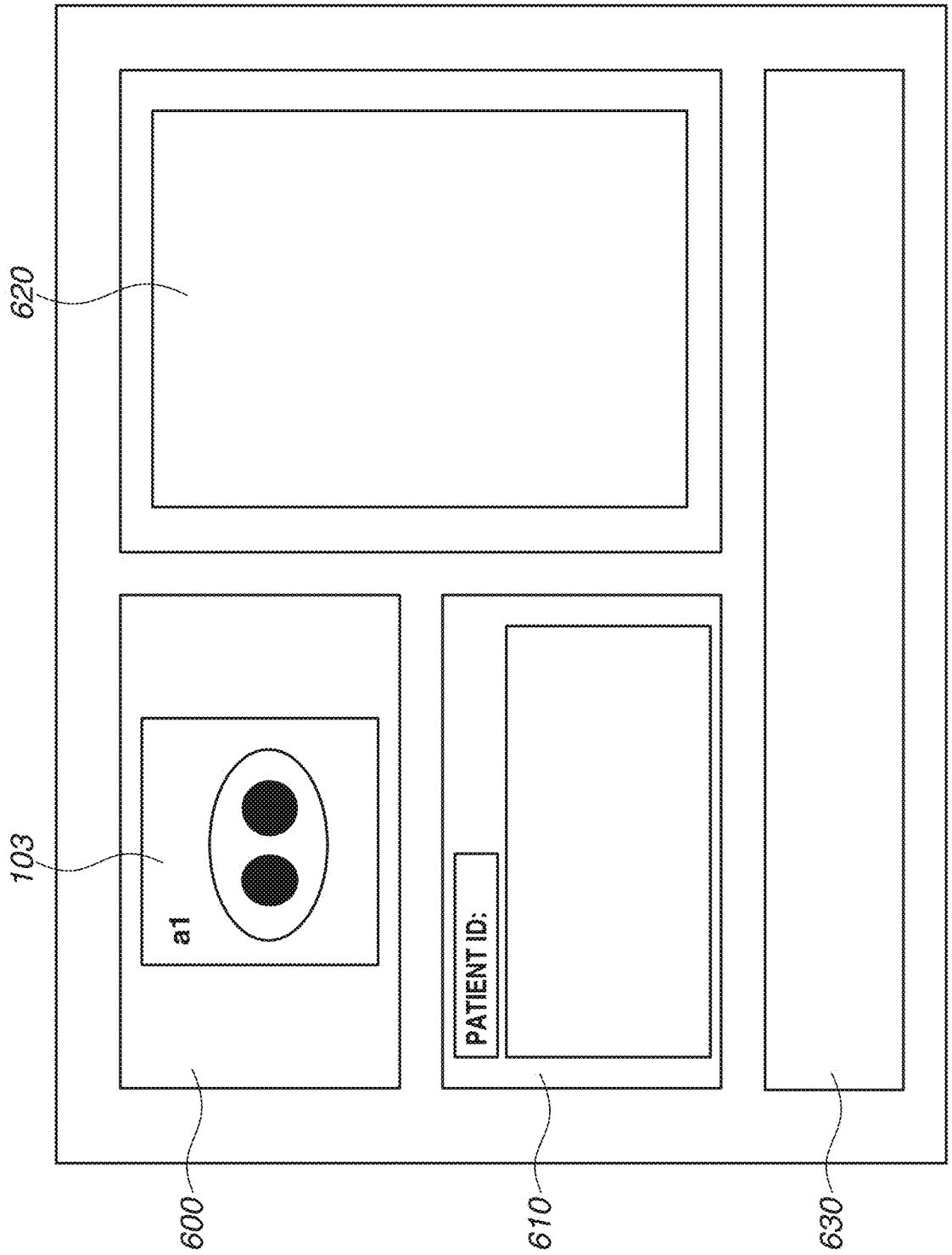
FIG. 15 illustrates a screen example after the medical information is displayed according to an exemplary modification 5.
Figure 16:
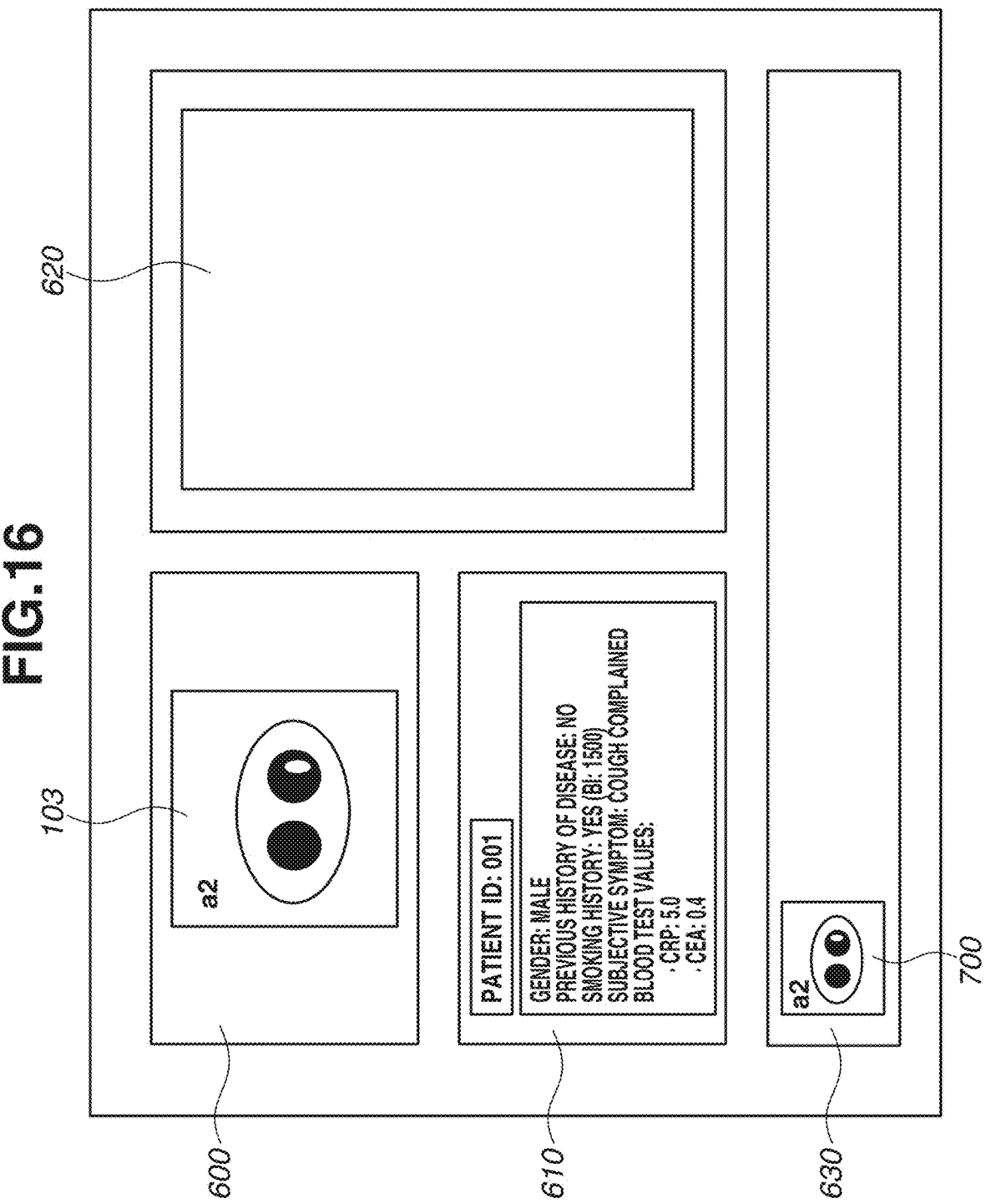
FIG. 16 illustrates a screen example after the representative image is displayed according to the exemplary modification 5.

FIGS. 15, 16, and 18 are diagrams each illustrating a screen example on the display unit 36. A region 600 indicates a region where information acquired by the medical image display device is displayed. A region 610 indicates a region where information acquired by a clinical information display device is displayed. A region 620 indicates a region where information acquired by a radiological interpretation report device is displayed. A region 630 indicates a region where information acquired by a representative image display device is displayed.

The clinical information display device is a device that reads out various kinds of clinical information and examination information stored in the electronic medical record system and the like from the database 22 and displays the read information according to the user's instruction. The radiological interpretation report device is a device that generates and displays a radiological interpretation report generated at the time of the diagnostic imaging task. The representative image display device is a device that displays the representative image generated by the representative information generation unit 44.

A processing procedure according to the present exemplary modification will be sequentially described using a specific example. A flowchart according to the present exemplary modification is similar to FIG. 2.

In step S200, the user operates the medical image display device to display the slice image a1 of the medical image 103 of a patient having a patient identification (ID) of 001 in the region 600. Since the user issues the instruction "display the medical image 103" to the medical image display device at this time, the processing proceeds to step S210. FIG. 15 illustrates a screen example on the display unit 36 when the present operation ends.

In step S210, the processing from steps S210 to S250 is not performed with respect the instruction issued for the first time at the time of the diagnostic imaging in the present exemplary modification, either. Therefore, the processing proceeds to step S260. Because the user does not issue the instruction to end the diagnostic imaging in step S260 (NO in step S260), the processing returns to step S200.

After the processing returns to step S200, the user next issues the instruction "carry out the function of advancing to the next slice" with respect to the medical image 103 to change the slice image which is displayed in the region 600 from a1 to a2. Since the user issues the instruction "carry out the function of advancing to the next slice" at this time, the processing proceeds to step S210.

In step S210, the display content storage unit 42 acquires the display content in the region 600 at a time point immediately before a time point at which the instruction "carry out the function of advancing to the next slice" has been executed, and stores the reproduction information thereof into the storage unit 34. In the present exemplary modification, the display content storage unit 42 acquires and stores the capture image of the slice image a1 and the display time period of the slice image a1 (assumed to be two seconds) as the reproduction information.

In step S220, the user instruction determination unit 41 determines whether the user's instruction "carry out the function of advancing to the next slice" satisfies the determination condition. Suppose that the determination condition in the present exemplary modification is a condition "the determination target instruction is an instruction to change the medical information display device to which the instruction is directed". The instruction "carry out the function of advancing to the next slice" does not satisfy this determination condition. Therefore, the processing returns to step S200.

After the processing returns to step S200, the user next operates the clinical information display device to display clinical information of the patient having the patient ID of 001 in the region 610. Since the user issues the instruction "change the instruction target to the clinical information display device and display the clinical information" at this time, the processing proceeds to step S210.

In step S210, the display content storage unit 42 acquires the display content at a time point immediately before a time point at which the instruction "change the instruction target to the clinical information display device and display the clinical information" has been executed. Since the instruction has issued to the clinical information display device for the first time at this time, nothing is displayed on the clinical information display device at the time point immediately before the time point at which this instruction has been executed. In such a case, the display content storage unit 42 acquires the display content on the device (the medical image display device in the present example) operated at the time point before the instruction target device (the clinical information display device in the present example), at the time point immediately before the time point at which this instruction has been executed. In other words, in the present exemplary modification, the display content storage unit 42 acquires and stores the capture image of the slice image a2 and the display time period of the slice image a2 (assumed to be five seconds) as the reproduction information.

In step S220, the user instruction determination unit 41 determines whether the user's instruction "change the instruction target to the clinical information display device and display the clinical information" satisfies the determination condition. The determination condition in the present exemplary embodiment includes the condition "the determination target instruction is the instruction to change the medical information display device to which the instruction is issued", and the instruction "change the instruction target to the clinical information display device and display the clinical information" satisfies this determination condition. Therefore, the processing proceeds to step S230. Hereinafter, reproduction information formed from a pair of the capture image a1 acquired in the present exemplary modification and the display time period corresponding thereto (two seconds) will be referred to as $\inf_{300}$. Similarly, reproduction information formed from a pair of the capture image a2 and the display time period corresponding thereto (five seconds) will be referred to as $\inf_{310}$.

In step S230, the group generation unit 43 reads out the pieces of reproduction information stored during the predetermined time period from the display content storage unit 42, and groups them. The criterion for determining the start point of the grouping time period in the present exemplary embodiment is set to the "execution time point of the instruction that has satisfied the determination condition last time" or the "execution time point of the instruction that has been issued for the first time". The criterion for determining the end point of the grouping time period is set to the "time point immediately before the execution time point of the instruction that has satisfied the determination condition this time". In other words, the grouping time period in the present exemplary modification is set to a time period since the "execution time point of the instruction to display the medical image 103" until the "time point immediately before the execution time point of the instruction to change the instruction target to the clinical information display device and display the clinical information". Therefore, the group generation unit 43 groups the two pieces of reproduction information $inf_{300}$ and $inf_{310}$ as one group, as the reproduction information of this grouping time period.

In step S240, the representative information generation unit 44 identifies the representative display content of the group. The criterion for identifying the representative display content in the present exemplary modification is set to "select the display content displayed for the longest time period as the representative display content". More specifically, the representative information generation unit 44 compares the display time periods in the two pieces of reproduction information $inf_{300}$ and $inf_{310}$ to identify the representative display content. In the case of the present exemplary modification, the display time period in $inf_{310}$ is five seconds and is longest, and therefore the display content corresponding to $inf_{310}$ is selected as the representative display content. Next, the representative information generation unit 44 acquires the capture image of this display content (the capture image of the slice image a2 in this case) from $inf_{310}$. Then, the representative information generation unit 44 converts this capture image into a size suitable to be displayed on the representative image display device. The capture image of the slice image a2 after the conversion processing will be referred to as a representative image 700.

In step S250, the representative image 700 is displayed in the region 630. FIG. 16 illustrates a screen example on the display unit 36 after the present step. The slice image a2 of the medical image 103 of the patient having the patient ID of 001 is displayed in the region 600. The clinical information of this patient is displayed in the region 610. Then, the representative image 700 is displayed in the region 630.

Because the user does not issue the instruction to end the diagnostic imaging in step S260 (NO in step S260), the processing returns to step S200. After the processing returns to step S200, the user next operates the radiological interpretation report device to write the radiological interpretation report. Since the user issues an instruction "change the instruction target to the radiological interpretation report device and write the radiological interpretation report" at this time, the processing proceeds to step S210.

In step S210, the display content storage unit 42 acquires the display content at a time point immediately before a time point at which the instruction "change the instruction target to the radiological interpretation report device and write the radiological interpretation report" has been executed. Since the instruction has issued to the radiological interpretation report device for the first time at this time, nothing is displayed on the radiological interpretation report device at the time point immediately before the time point at which this instruction has been executed. Therefore, the display content storage unit 42 acquires the display content on the device (the clinical information display device in the present example) operated at the time point before the instruction target device (the radiological interpretation report device in the present example), at the time point immediately before the time point at which this instruction has been executed. In other words, the display content storage unit 42 acquires and stores the display information data on the clinical information display device and a display time period corresponding thereto (thirty seconds) as the reproduction information.

In step S220, the user instruction determination unit 41 determines whether the user's instruction "change the instruction target to the radiological interpretation report device and write the radiological interpretation report" satisfies the determination condition. From the above-described condition, the user's instruction "change the instruction target to the radiological interpretation report device and write the radiological interpretation report" satisfies the determination condition. Therefore, the processing proceeds to step S230. Hereinafter, a pair of the display information data on the clinical information display device and the display time period of thirty seconds that are acquired in the present exemplary modification will be referred to as $inf_{320}$.

In step S230, the group generation unit 43 reads out the pieces of reproduction information stored during the grouping time period, and groups them. Based on the above-described criteria, the grouping time period is set to a time period since the "execution time point of the instruction to change the instruction target to the clinical information display device and display the clinical information" until the "time point immediately before the execution time point of the instruction to change the instruction target to the radiological interpretation report device and write the radiological interpretation report". Therefore, the group generation unit 43 groups $inf_{320}$ as one group, as the reproduction information of this grouping time period.

In step S240, the representative information generation unit 44 generates the representative image of the group generated in step S230. This group contains only $inf_{320}$, so that the display content corresponding to $inf_{320}$ is selected as the representative display content. The display content corresponding to $inf_{320}$ is the display information data on the clinical information display device. First, the representative information generation unit 44 reproduces the display content from this display information data, and generates the representative image indicating the reproduced display content. The representative image generated by simply reproducing the display content can make it difficult for the user to understand the main point of the display content, like information mainly containing text information displayed on the clinical information display device in the present example. Such a case can be dealt with by using an image expressing information simplifying the display content as the second representative image.

Figure 17:
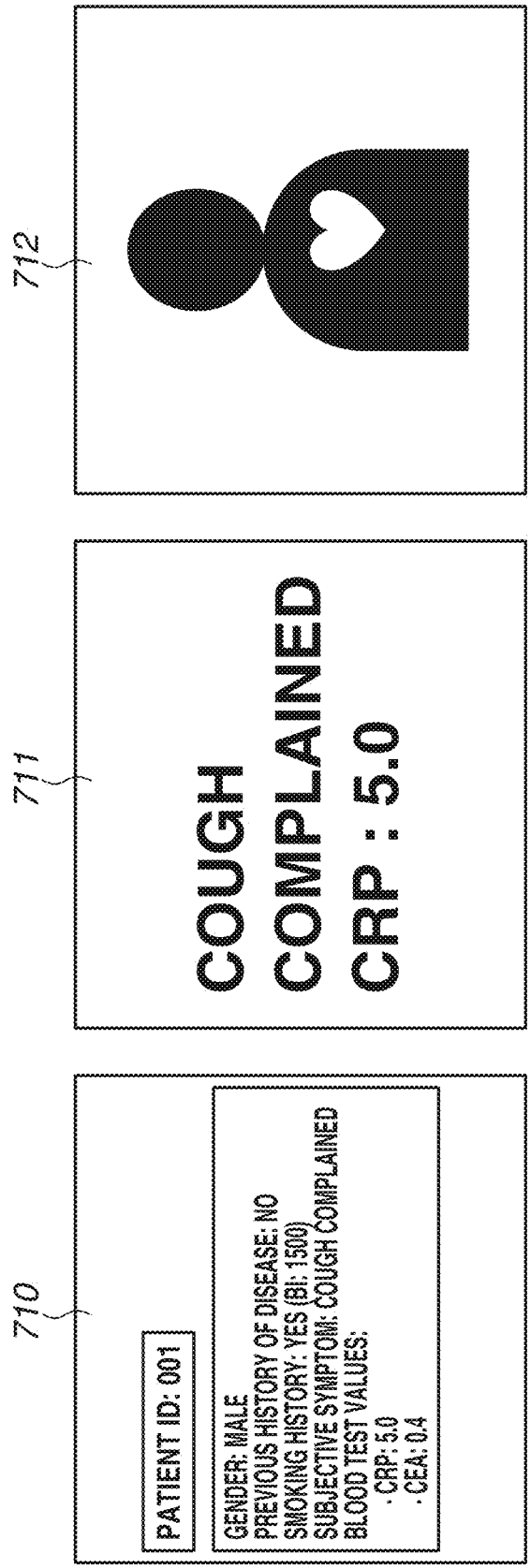
FIG. 17 illustrates examples of a second representative image.

Examples of the second representative image are indicated using FIG. 17. A representative image 710 is an image generated by reproducing the display content corresponding to $inf_{320}$. A representative image 711 is an image generated by extracting a summary of the text information from the text information with use of a known technique and displaying only the extracted summary. A representative image 712 is an image displaying an icon expressing a schematic representation of the clinical information display device. Then, in the present example, the representative image 712, which is the icon simplifying the present representative image, is utilized as the second representative image.

In step S250, the second display control unit 45 displays the representative image 712 on the representative image display device. FIG. 18 illustrates a screen example on the display unit 36 after the present step. The slice image a2 of the medical image 103 of the patient having the patient ID of 001 is displayed on the medical image display device. The clinical information of this patient is displayed on the clinical information display device. The radiological interpretation report written by the user is displayed on the radiological interpretation report device. Then, the representative image 700 and the representative image 712 are displayed on the representative image display device while being arranged in the chronological order from a left side to a right side of the drawing. In step S260, the user issues the instruction to end the diagnostic imaging. Therefore, the processing in the present exemplary embodiment ends.

Implementing the present exemplary modification enables the present exemplary embodiment to be employed even when the user engages in the diagnostic imaging task while displaying the plurality of types of medical information on the plurality of display devices.

In the present exemplary embodiment, the medical information processing apparatus 10 generates the representative image of the group and displays only the representative image in step S240. The medical information processing apparatus 10 can record other reproduction information of the group in association with this representative image, and display it based on the user's instruction.

This processing will be specifically described with reference to FIGS. 5 and 6. In step S230, the three pieces of reproduction information $inf_{200}$, $inf_{210}$, and $inf_{220}$ illustrated in FIG. 5 are grouped. In step S240, the capture image of the slice image a2 of $inf_{210}$ is selected as the representative image 300. In step S250, the representative image 300 is displayed in the representative information display region 102 as illustrated in FIG. 6. In this case, the three pieces of reproduction information $inf_{200}$, $inf_{210}$, and $inf_{220}$ are recorded in association with the representative image 300. Then, when the user selects the representative image 300, the three display contents of $inf_{200}$, $inf_{210}$, and $inf_{220}$ associated with the representative image 300 are sequentially displayed in the medical image display region 101 or the representative information display region 102.

Sequentially displaying only the reproduction information associated with each of the representative images in this manner enables the user to confirm the display content during a specific grouping time period alone. Therefore, the user can efficiently confirm the display content even when wanting to confirm the display content later. The user can confirm the actual instruction and display content in each of the work processes in the diagnostic imaging task, thereby also utilizing this configuration for an education of unskilled medical doctors.

Other Embodiments

The present exemplary embodiment can be implemented by combining two or more of the above-described exemplary modifications.

The above-described technique(s) can be implemented as an embodiment in the form of, for example, a system, an apparatus, a method, a program, or a recording medium (a storage medium). More specifically, the above-described technique(s) can be applied to a system including a plurality of devices, e.g., a host computer, an interface device, an imaging device, a web application, and the like, or can also be applied to an apparatus including one device.

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-256153, filed Dec. 28, 2016, which is hereby incorporated by reference herein in its entirety.

What is claimed is:

1. An information processing apparatus comprising:
a display control unit configured to control a display unit;
a storage unit configured to store medical information;
one or more processors; and
at least one memory storing executable instructions, which when executed by the one or more processors, cause the information processing apparatus to:
display first pieces of medical information, by the display control unit, in a first region on the display unit based on a first instruction that is based on a first user input;
display second pieces of medical information, by the display control unit, in the first region on the display unit based on a second instruction that is based on a second user input, the second instruction comprising an instruction to change content displayed in the first region on the display unit;
display third pieces of medical information, by the display control unit, in the first region on the display unit based on a third instruction that is based on a third user input, the third instruction comprising an instruction to change content displayed in the first region on the display unit;
determine whether the second instruction and the third instruction satisfy a predetermined condition including at least one of changing an observation target, performing a density conversion function and terminating a diagnostic imaging;
generate a first group of the first pieces of medical information that have been displayed on the display unit during a time period between the first instruction and the second instruction in response to determining that the second instruction satisfy the predetermined condition, and a second group of the second pieces of medical information that have been displayed on the display unit during a time period between the second instruction and the third instruction in response to determining that the second instruction and the third instruction satisfy the predetermined condition;
identify a first representative of the first pieces of medical information in the first group based on one or more criteria from among the first pieces of medical information, and a second representative of the second pieces of medical information in the second group based on one or more criteria from among the second pieces of medical information;

generate first representative medical information based on the first representative of the first pieces of medical information in the first group, and second representative medical information based on the second representative of the second pieces of medical information in the second group; and automatically display the generated first representative medical information and the generated second representative medical information in chronological order, by the display control unit, in a second region on the display unit.

2. The information processing apparatus according to claim 1, wherein the second representative of the second pieces of medical information in the second group is identified based on time periods during which the second pieces of medical information contained in the second group are displayed in the first region on the display unit.

3. The information processing apparatus according to claim 2, wherein the second representative of the second pieces of medical information is displayed in the first region on the display unit for a longest time period from among the second pieces of medical information contained in the second group.

4. The information processing apparatus according to claim 1, wherein the executable instructions, when executed by the one or more processors, further cause the information processing apparatus to:

not generate the second representative medical information if a number of the second pieces of medical information contained in the second group is less than or equal to a threshold value.

5. The information processing apparatus according to claim 1, wherein the executable instructions, when executed by the one or more processors, further cause the information processing apparatus to:

not display the second representative medical information if a number of the second pieces of medical information contained in the second group is less than or equal to a threshold value.

6. The information processing apparatus according to claim 1, wherein the second group of the second pieces of medical information is grouped based on the second instruction and feature information of the medical information.

7. The information processing apparatus according to claim 6, wherein the feature information is information indicating a site of a subject contained in the medical information, and the second pieces of medical information are grouped in a case where the site of the subject is changed in the displayed second pieces of medical information.

8. The information processing apparatus according to claim 1, wherein the executable instructions, when executed by the one or more processors, further cause the information processing apparatus to:

display a plurality of pieces of representative medical information in the second region as a history of display operations, from a plurality of groups, on the display unit.

9. The information processing apparatus according to claim 1, wherein the second instruction to change the content displayed in the first region on the display unit includes an instruction to change a type of the medical information.

10. The information processing apparatus according to claim 1, wherein the medical information includes a medical image, and wherein the second instruction to change the content displayed in the first region on the display unit includes one or more of an instruction to change contrast with respect to the medical image, an instruction to change a magnification ratio of the medical image, an instruction to change a display cross section of the medical image, and an instruction to change a type of the medical image.

11. The information processing apparatus according to claim 1, wherein the second representative medical information includes one or more of the second representative of the second pieces of medical information itself, a capture image of the second representative of the second pieces of medical information displayed in the first region on the display unit, and information generated by performing image processing on the second representative of the second pieces of medical information.

12. The information processing apparatus according to claim 1, wherein the second group contains the second pieces of medical information displayed in the first region on the display unit during a period of time since receipt of the second instruction until receipt of the third instruction.

13. An information processing method comprising:

displaying first pieces of medical information, by a display control unit, in a first region on a display unit based on a first instruction that is based on a first user input;

displaying second pieces of medical information, by the display control unit, in the first region on the display unit based on a second instruction that is based on a second user input, the second instruction comprising an instruction to change content displayed in the first region on the display unit;

displaying third pieces of medical information, by the display control unit, in the first region on the display unit based on a third instruction that is based on a third user input, the third instruction comprising an instruction to change content displayed in the first region on the display unit;

determining whether the second instruction and the third instruction satisfy a predetermined condition including at least one of changing an observation target, performing a density conversion function and terminating a diagnostic imaging;

generating a first group of the first pieces of medical information that have been displayed on the display unit during a time period between the first instruction and the second instruction in response to determining that the second instruction satisfy the predetermined condition, and a second group of the second pieces of medical information that have been displayed on the display unit during a time period between the second instruction and the third instruction in response to determining that the second instruction and the third instruction satisfy the predetermined condition;

identifying a first representative of the first pieces of medical information in the first group based on one or more criteria from among the first pieces of medical information, and a second representative of the second pieces of medical information in the second group based on one or more criteria from among the second pieces of medical information;

generating first representative medical information based on the first representative of the first pieces of medical information in the first group, and second representative medical information based on the second representative of the second pieces of medical information in the second group; and automatically displaying the generated first representative medical information and the generated second representative medical information in chronological order, by the display control unit, in a second region on the display unit.

14. A non-transitory computer-readable storage medium storing a program for causing a computer to execute a method, the method comprising:

displaying first pieces of medical information, by a display control unit, in a first region on a display unit based on a first instruction that is based on a first user input;

displaying second pieces of medical information, by the display control unit, in the first region on the display unit based on a second instruction that is based on a second user input, the second instruction comprising an instruction to change content displayed in the first region on the display unit;

displaying third pieces of medical information, by the display control unit, in the first region on the display unit based on a third instruction that is based on a third user input, the third instruction comprising an instruction to change content displayed in the first region on the display unit;

determining whether the second instruction and the third instruction satisfy a predetermined condition including at least one of changing an observation target, performing a density conversion function and terminating a diagnostic imaging;

generating a first group of the first pieces of medical information that have been displayed on the display unit during a time period between the first instruction and the second instruction in response to determining that the second instruction satisfy the predetermined condition, and a second group of the second pieces of medical information that have been displayed on the display unit during a time period between the second instruction and the third instruction in response to determining that the second instruction and the third instruction satisfy the predetermined condition;

identifying a first representative of the first pieces of medical information in the first group based on one or more criteria from among the first pieces of medical information, and a second representative of the second pieces of medical information in the second group based on one or more criteria from among the second pieces of medical information;

generating first representative medical information based on the first representative of the first pieces of medical information in the first group, and second representative medical information based on the second representative of the second pieces of medical information in the second group; and automatically displaying the generated first representative medical information and the generated second representative medical information in chronological order, by the display control unit, in a second region on the display unit.

15. The information processing apparatus according to claim 1, wherein determining whether the second instruction satisfies the predetermined condition comprises determining whether the second instruction is an instruction serving to separate work processes.

16. The information processing apparatus according to claim 15, wherein the instruction serving to separate work processes includes at least one of an instruction to change the observation target, an instruction to carry out the density conversion function, and an instruction to end the diagnostic imaging.

17. The information processing apparatus according to claim 1, wherein the executable instructions, when executed by the one or more processors, further cause the information processing apparatus to:

display a plurality of pieces of representative medical information in chronological order in the second region; and move the plurality of pieces of representative medical information in the second region based on one or more user inputs received via a user interface such that one or more of the plurality of pieces of representative medical information are no longer displayed in the second region.

18. The information processing apparatus according to claim 1, wherein the executable instructions, when executed by the one or more processors, further cause the information processing apparatus to:

determine whether to store one of the second pieces of medical information based on one or more criteria, wherein the second group of the second pieces of medical information does not include the one of the second pieces of medical information in a case that it is determined not to store the one of the second pieces of medical information.

* * * * *